(12) United States Patent
Godfrey et al.

(10) Patent No.: US 9,187,727 B2
(45) Date of Patent: *Nov. 17, 2015

(54) METHODS FOR THE ISOLATION AND EXPANSION OF CORD BLOOD DERIVED T REGULATORY CELLS

(75) Inventors: Wayne R. Godfrey, Los Altos, CA (US); Carl June, Merion Station, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/544,218

(22) Filed: Jul. 9, 2012

(65) Prior Publication Data

US 2012/0282694 A1 Nov. 8, 2012

Related U.S. Application Data

(63) Continuation of application No. 11/226,168, filed on Sep. 14, 2005.

(60) Provisional application No. 60/609,916, filed on Sep. 15, 2004.

(51) Int. Cl.
C12N 5/071 (2010.01)
C12N 5/00 (2006.01)
C12N 5/0783 (2010.01)

(52) U.S. Cl.
CPC ............ *C12N 5/0087* (2013.01); *C12N 5/0636* (2013.01); *C12N 2501/23* (2013.01); *C12N 2501/505* (2013.01); *C12N 2501/515* (2013.01); *C12N 2501/599* (2013.01)

(58) Field of Classification Search
None
See application file for complete search history.

(56) References Cited

U.S. PATENT DOCUMENTS

2003/0147865 A1 8/2003 Salomon et al.
2005/0196386 A1* 9/2005 Blazar et al. ................. 424/93.7

OTHER PUBLICATIONS

Apostolou, et al., "Origin of regulatory T cells with known specificity for antigen," Nat Immunol 3(8):756-763 (2002).
Asseman, et al., "An essential role for interleukin 10 in the function of regulatory T cells that inhibit intestinal inflammation," J Exp Med 190(7):995-1004 (1999).
Baecher-Allan et al., "CD4+CD25 high regulatory cells in human peripheral blood," J. Immunol. 167:1245-1253 (2001).
Baecher-Allan et al., "Human CD4+CD25+ regulatory T cells." Semin Immunol. Apr. 2004; 16(2):89-98.
Barker and Wagner, "Umbilical cord blood transplantation: current practice and future innovations." Crit Rev Oncol Hematol. Oct. 2003;48(1):35-43.
Belkaid, et al., "CD4+CD25+ regulatory T Cells control Leishmania major persistence and immunity," Nature 420(6915):502-507 (2002).
Cella, et al., "Maturation, activation, and protection of dendritic cells induced by double-stranded RNA," J Exp Med 189(5):821-829 (1999).
Chen and Wahl, "TGF-beta: the missing link in CD4+CD25+ regulatory T cell-mediated immunosuppression." Cytokine Growth Factor Rev. Apr. 2003; 14(2):85-89.
Cohen, et al., "CD4(+)CD25(+) immunoregulatory T cells: new therapeutics for graft-versus-host disease," J Exp Med 196(3):401-406 (2002).
Edinger, et al., "CD4+CD25+ regulatory T cells preserve graft-versus-tumor activity while inhibiting graft-versus-host disease after bone marrow transplantation," 9(9):1144-1150 (2003).
Fujimaki et al., "Comparative study of regulatory T cell function of human CD25CD4 T cells from thymocytes, cord blood, and adult peripheral blood." 2008, Clin Dev Immunol 2008: 305859.
Gallimore and Sakaguchi, "Regulation of tumour immunity by CD25+ T cells," Immunology 107(10):5-9 (2002).
Gavilondo et al., "Antibody Engineering at the Millennium." 2000, Biotechniques 29:128-145.
Godfrey et al., 2003, "Generation of human CD4+CD25+ suppressor cell lines which markedly inhibit HLA mismatched dentritic cell stimulated MLR." Blood, vol. 102, No. 11, p. 947a (Abstract).
Godfrey et al., "Cord blood CD4(+)CD25(+)-derived T regulatory cell lines express FoxP3 protein and manifest potent suppressor function." 2005, Blood 105(2):750-58.
Godfrey, et al., "Ex vivo depletion of alloreactive cells based on CFSE dye dilution, activation antigen selection, and dendritic cell stimulation," Blood 103:1158-1165 (Feb. 2004).
Godfrey, et al., "In vitro expanded human CD4+CD25+ T regulatory cells can markedly inhibit allogeneic dendritic cell stimulated MLR cultures," Blood 104(2):453-461 (Jul. 15, 2004).
Grindebacke et al., "Dynamic Development of Homing Receptor Expression and Memory Cell Differentiation of Infant CD4+CD25high Regulatory T Cells." 2009, J Immunol 183(7):4360-70.
Hall, et al., "Anti-CD4 monoclonal antibody-induced tolerance to MHC-incompatible cardiac allografts maintained by CD4+ suppressor T cells that are not dependent upon IL-4," 161(10):5147-5146 (1998).
Hoffmann et al., "Large Scale In Vitro Expansion of Polyclonal Human CD4+CD25high Regulatory T Cells." Blood. 2004;104(3):895-903.
Hoffmann, et al.,"Donor-type CD4(+)CD25(+) regulatory T cells suppress lethal acute graft-versus-host disease after allogeneic bone marrow transplantation," J Exp Med 196(3):389-399 (2002).
Ji et al. "The natural ligand for glucocorticoid-induced TNF receptor-related protein abrogates regulatory T cell suppression." J Immunol. May 15, 2004;172(10):5823-5827.
Jones, et al., "Post-hematopoietic cell transplantation control of graft-versus-host disease by donor CD425 T cells to allow an effective graft-versus-leukemia response," Biol Blood Marrow Transplant 9(4):243-256 (2003).
Jonuleit et al., "Induction of interleukin 10-producing, nonproliferating CD4(+) T cells with regulatory properties by repetitive stimulation with allogeneic immature human dendritic cells." J Exp Med. Nov. 6, 2000;192(9):1213-1222.
Kaminski et al., "Reduced expression of NFAT-associated genes in UCB versus adult CD4+ T lymphocytes during primary stimulation." Blood. Dec. 15, 2003;102(13):4608-4617.

(Continued)

*Primary Examiner* — Amy Juedes
(74) *Attorney, Agent, or Firm* — Saul Ewing LLP; Kathryn Doyle; Kelly J. Morgan

(57) ABSTRACT

The present invention encompasses methods, and kits for the isolation and expansion of T regulatory cells having the CD45RA+ phenotype, including such cells from human umbilical cord blood.

7 Claims, 18 Drawing Sheets

(56) References Cited

OTHER PUBLICATIONS

Levine et al., "Large-scale production of CD4+ T cells from HIV-1-infected donors after CD3/CD28 costimulation." J Hematother. Oct. 1998;7(5):437-48.

Levings et al., "Human CD25+CD4+ T suppressor cell clones produce transforming growth factor beta, but not interleukin 10, and are distinct from type 1 T regulatory cells," J. Exp. Med. 196:1335-1346 (2002).

Levings et al., "Human cd25(+)cd4(+) t regulatory cells suppress naive and memory T cell proliferation and can be expanded in vitro without loss of function." 2001, J Exp Med 193:1295-1301.

Lin et al., "Efficient expansion of regulatory T cells in vitro and in vivo with a CD28 superagonist." 2003, Eur J Immunol 33:626-638.

McHugh et al., "CD4(+)CD25(+) immunoregulatory T cells: gene expression analysis reveals a functional role for the glucocorticoid-induced TNF receptor." Immunity. Feb.2002; 16(2):311-323.

Nakamura et al. "TGF-beta 1 plays an important role in the mechanism of CD4+CD25+ regulatory T cell activity in both humans and mice." J Immunol. J. 15, 2004;172(2):834-842.

Ng, et al., "Human CD4(+)CD25(+) cells: a naturally occurring population of regulatory T cells," Blood 98(9):2736-2744 (2001).

Paganelli, et al., "Activated and "memory" phenotype of circulating T lymphocytes in intrauterine life." Cell Immunol. May 1994; 155(2):486-489.

Peng, et al., "Tumor-induced L-selectin high suppressor T cells mediate potent effector T cell blockade and cause failure of otherwise curative adoptive immunotherapy," J. Immunol 169(9): 4811-4821 (2002).

Ramsdell and Ziegler, "Transcription factors in autoimmunity." Curr Opin Immunol. Dec. 2003; 15(6):718-24.

Sakaguchi et al., "Immunologic self-tolerance maintained by activated T cells expressing IL-2 receptor alpha-chains (CD25). Breakdown of a single mechanism of self-tolerance causes various autoimmune diseases." J. Immunol. 155:1151-1164 (1995).

Sakaguchi, "Naturally arising CD4 regulatory T cells for immunologic self-tolerance and negative control of immune responses," Annu Rev Immunol ;22:531-62 (2004).

Sallusto and Lanzavecchia, "Efficient presentation of soluble antigen by cultured human dendritic cells is maintained by granulocyte/macrophage colony-stimulating factor plus interleukin 4 and downregulated by tumor necrosis factor alpha," J Exp Med 179(4):1109-1118 (1994).

Shevach, "CD4+ CD25+ suppressor T cells: more questions than answers," Nat. Rev. Immunol. 2:389-400 (2002).

Shevach, "Regulatory T cells in autoimmmunity," Annu. Rev. Immunol. 18:423-449 (2000).

Shevach, et al., "Control of T-cell activation by CD4+CD25+ suppressor T cells," Immunol Rev 182:58-67 (2001).

Spisek, et al., "Standardized generation of fully mature p70 IL-12 secreting monocyte-derived dendritic cells for clinical use," Cancer Immunol Immunother 50(8):417-421 (2001).

Takahata et al., "CD25+CD4+ T cells in human cord blood: an immunoregulatory subset with naive phenotype and specific expression of forkhead box p3 (Foxp3) gene." 2004, Exp Hematol 32(7):622-9.

Takeda et al.,"Distinct roles for the OX40-OX40 ligand interaction in regulatory and nonregulatory T cells." J Immunol. Mar. 15, 2004;172(6):3580-3589.

Tang et al., "In Vitro-expanded Antigen-specific Regulatory T Cells Suppress Autoimmune Diabetes," J Exp Med. 2004 199(11):1455-1465.

Taylor, et al., "The infusion of ex vivo activated and expanded CD4(+)CD25(+) immune regulatory cells inhibits graft-versus-host disease lethality," Blood 99(10):3493-3499 (2002).

Thornton and Shevach "CD4+CD25+ immunoregulatory T cells suppress polyclonal T cell activation in vitro by inhibiting interleukin 2 production," J. Exp. Med. 188:287-296 (1998).

Thornton et al., "Functional maturation of CD4+CD25+CTLA4+CD45RA+ T regulatory cells in human neonatal T cell responses to environmental antigens/allergens." 2004, J. Immunology 173: 3084-3092.

Trenado, et al., "Recipient-type specific CD4+CD25+ regulatory T cells favor immune reconstitution and control graft-vesus-host disease while maintaining graft-versus-leukemia," J Clin Invest 112(11):1688-1696 (2003).

Wadlow and Porter, "Umbilical cord blood transplantation: where do we stand?" Biol Blood Marrow Transplant. 2002;8(12):637-647.

Wing et al., "Characterization of human CD25+ CD4+ T cells in thymus, cord and adult blood." Immunology. Jun. 2002; 106(2):190-199.

Wing et al., "CD4+ CD25+ FOXP3+ regulatory T cells from human thymus and cord blood suppress antigen-specific T cell responses." 2005, Immunology 115:516-525.

Wing et.al., "CD4 T cell activation by myelin oligodendrocyte glycoprotein is suppressed by adult but not cord blood CD25+ T cells." Eur J Immunol. Mar. 2003;33(3):579-87.

Wood and Sakaguchi, "Regulatory T cells in transplantation tolerance," Nat Rev Immunol 3(3):199-210 (2003).

\* cited by examiner

METHODS FOR THE ISOLATION AND EXPANSION OF CORD BLOOD DERIVED T REGULATORY CELLS

CROSS-REFERENCE TO RELATED APPLICATIONS

The present application is a continuation of U.S. patent application Ser. No. 11/226,168, filed Sep. 14, 2005, pending, which claims priority pursuant to 35 U.S.C. §119(e) to U.S. Provisional Application No. 60/609,916, filed Sep. 15, 2004, each of which is hereby incorporated by reference in its entirety herein.

GOVERNMENT INTERESTS

This invention was supported in part by the National Institutes of Health Grant Nos. R01 AI34495 and R37 HL56067. The Government has certain rights in this invention.

FIELD OF THE INVENTION

The present invention relates to T regulatory ($T_{reg}$) cells isolated from human cord blood, as well as compositions, methods and kits using $T_{reg}$ cells so isolated.

BACKGROUND OF THE INVENTION

Naturally arising $CD4^+CD25^+$ T regulatory cells ($T_{reg}$) can restrict or alter most types of immune responses (Sakaguchi, 2004, *Annu. Rev. Immunol.*, 22: 531-562). Initially, $T_{reg}$ cells were described to be critical for the control of autoimmunity (Sakaguchi, et al., 1995, *J. Immunol.*, 155: 1151-1164; Shevach, 2000, *Annu. Rev. Immunol.*, 18: 423-449), and were found on adoptive transfer to prevent experimental autoimmune diseases. More recently, $T_{reg}$ have been shown to suppress allogeneic immune responses, and can prevent transplant rejection (Hall, et al., 1998, *J. Immunol.*, 161: 5147-5156; Wood, et al., 2003, *Nat. Rev. Immunol.*, 3: 199-210). In addition, these cells can restrain anti-tumor (Peng L, et al., 2002, *J. Immunol.*, 169: 4811-4821; Gallimore, et al., 2002, *Immunology*, 107: 5-9), and anti-microbial immune responses (Belkaid Y, et al., 2002, *Nature*, 420: 502-507). Thus, $CD4^+CD25^+$ $T_{reg}$ appear to be central control elements of immunoregulation, and understanding their biology is important to efforts aimed at therapeutically manipulating immune responses.

$T_{reg}$ cells are best characterized in mice where they constitute 5-10% of lymph node and spleen $CD4^+$ T-cell populations. They are generated both through central thymic developmental mechanisms in pathogen free mice, and also arise by poorly defined peripheral generation or expansion mechanisms (Apostolou, et al., 2002, *Nat. Immunol.*, 3: 756-763; Shevach et al., 2002, *Nat. Rev. Immunol.*, 2: 389-400). To date, $T_{reg}$ cells have primarily been defined by co-expression of $CD4^+$ and $CD25^+$ antigens on fresh isolation. CD25 as well as other markers of murine $T_{reg}$, CTLA4 (CD 152) and GITR (Glucocorticoid Induced TNF-like Receptor), are all activation antigens on conventional T cells, and therefore are not specific. FoxP3, a nuclear protein thought to function as a transcriptional repressor, is a newer marker considered to be more specific for $T_{reg}$ cells (Ramsdell, et al., 2003, *Curr. Opin. Immunol.*, 15: 718-24). It was demonstrated that after activation (T cell receptor based, antigen-specific or anti-CD3), $T_{reg}$ cells can non-specifically suppress proliferation of both $CD4^+$ and $CD8^+$ T cells. The mechanism of suppression is unclear, and in vitro, appears to require cell-cell contact. A functional result of suppression is impaired production of IL-2 (Thornton, et al., 1998, *J. Exp. Med.*, 188: 287-296; Shevach, et al., 2001, *Immunol. Rev.*, 182: 58-67). In vivo, the suppression mechanism is more controversial with some studies demonstrating dependence on immunosuppressive cytokines (Asseman, et al., 1999, *J. Exp. Med.*, 190: 995-1004), which are not required for in vitro suppression.

Studies in mouse models of bone marrow transplantation (BMT) have shown that fresh or culture expanded $CD4^+CD25^+$ cells can delay or prevent disease (Taylor et al., 2002, *Blood*, 99: 3493-3499' Hoffmann, et al., 2002, *J. Exp. Med.*, 196: 389-399; Cohen, et al., 2002, *J. Exp. Med.*, 196: 401-406). Previous studies have demonstrated that $T_{reg}$ polyclonally expanded ex vivo for 10 days with anti-CD3 plus IL-2, can be effective in preventing graft versus host disease (GVHD; Taylor, et al., 2002, *Blood*, 99: 3493-3499). Ex vivo expansion of $T_{reg}$ cells with irradiated allogeneic APCs plus exogenous IL-2 is also effective at suppressing GVHD (Cohen, et al., 2002, *J. Exp. Med.*, 196: 401-406). In some model systems, $T_{reg}$ cells can prevent GVHD and still allow for graft versus leukemia (GVL) effects (Edinger, et al., 2003, *Nat. Med.*, 9: 1144-1150; Jones, et al., 2003, *Biol. Blood Marrow Transplant*, 9: 243-56; Trenado, et al., 2003, *J. Clin. Invest.*, 112: 1688-96). In addition, studies in mouse models of autoimmune disease have demonstrated that culture expanded antigen specific (transgenic TCR) $CD4^+CD25^+$ cells can prevent or even treat diabetes (Tang, et al., 2004, *J. Exp. Med.*, 199: 1455-1465). Consequently, $T_{reg}$ cells have a role in clinical immunosuppressive therapy in transplantation, provided human $T_{reg}$ cells can be isolated and expanded in culture to generate sufficient numbers for in vivo infusion.

While the murine data are very promising, there still remains a practical problem of isolating pure $T_{reg}$ from human blood. In young mice, $CD4^+CD25^+$ cells are moderately abundant and the $CD25^+$ subset is readily apparent. In humans the $CD25^+$ cells are not as discrete of a population, as there exists a large and overlapping population of CD25-dim cells. It is possible that the co-purification of conventional T cells with $T_{reg}$ is the basis for the modest or variable suppressor activity observed in studies of human $CD4^+CD25^+$ cells (Baecher-Allan, et al., 2004, *Semin. Immunol.*, 16: 89-98). FACS cell sorting of the highest 1.7% of $CD25^+$ expressors ($CD25^{high}$ cells) has been reported to enable suppressor cell isolation (Baecher-Allan, et al., 2001, *J. Immunol.*, 167: 1245-1253). A stringent magnetic bead based approach was required to isolate populations of adult blood derived $T_{reg}$ cells pure enough for $CD4^+CD25^+$ cells to generate potent suppressor cell lines. Even so, strongly suppressive cell lines could only be generated in a subset (approximately one third) of donors, and potency correlated with cell line purity (Godfrey, et. al., 2004, *Blood*, 104: 453-461). FACS sorting of $CD25^{high}$ cells (top 2.1%) has been reported to enable more consistent suppressor cell line generation from adult blood (Hoffmann, et al., 2004, *Blood*. 104: 895-903).

Purification of $T_{reg}$ cells from adult blood is possible, but difficult. Previous attempts using magnetic activated cell sorting (MACS) purification to isolate $T_{reg}$ cells from adult blood that are sufficiently pure for consistent suppressor activity have resulted in variability in cell function. This variability is largely due to the presence of CD25-dim memory cells which overlap with $T_{reg}$ cells. Use of a cell sorter has facilitated the isolation of $T_{reg}$ cells (Baecher-Allan, et al., 2001, *J. Immunol.*, 167: 1245-1253), and enabled the generation of suppressor cell lines from adult blood (Hoffmann, et al., 2004, *Blood*, 104: 895-903). However, even sorted populations of adult blood derived $CD25^+$ cells (top 2.9%) were found in one report to contain a mix of conventional and regulatory T cells on cloning and functional analysis (Levings, et. al., 2002, *J. Exp. Med.,* 196: 1335-1346).

About 20% of of the CD4$^+$CD25$^+$ adult blood cells express CD45RA. This antigen is not expected to be expressed on suppressor cells, as they have been described in several reports to be CD45RO positive (generally mutually exclusive expression, except for transiently during activation of naïve cells). However, the isolation of these cells was much better than the CD45RA$^-$ cells for generating suppressor cell lines (12/12 cell lines isolated by this method were found to be potent suppressors). On naïve T cells the CD45RA splice variant is expressed on the T cell surface. Once a T cell differentiates into a memory cell, it usually expresses the CD45RO isoform (U.S. Publication No. 20050196386).

Cord blood has previously been shown to contain CD4$^+$ CD25$^+$ cells by fluorescence activated cells sorting (FACS) (Paganelli, et. al., 1994, *Cell Immunol.,* 155: 486-489; Ng, et al., 2001, *Blood* 98: 2736-2744; Wing, et al., 2002, *Immunology* 106: 190-199). However, there is minimal data reported on the function of these cells. One report has inferred suppressive function based on LDA frequency analysis (Ng, et al., 2001, *Blood* 98: 2736-2744). The only report evaluating functional activity of freshly isolated CD4$^+$CD25$^+$ cells, revealed no suppression of antigen specific responses. In addition, there was no increased antigen specific reactivity of CD4$^+$ cells after CD25$^+$ cell depletion. However, modest suppression was noted in anti-CD3 based T-cell co-culture assays, (60% at 1/1 responder/suppressor cell ratio) (Wing, et al., 2003, *Eur. J. Immunol.,* 33: 579-587). Thus, previous studies indicated that most cord blood derived CD25$^+$ cells were not yet mature enough to be suppressive (Wing K, et al., 2003, *Eur. J. Immunol.* 33: 579-587).

Accordingly, until the present invention, the properties and benefits of T$_{reg}$ cells were recognized, but method to isolate and generate sufficient numbers of potent suppressor cells were unknown. Therefore, a recognized need for methods to isolate and expand T$_{reg}$ cells existed. The present invention meets this need.

SUMMARY OF THE INVENTION

The present invention includes a method for isolating a regulatory T cell from a population of phenotypically CD45RA$^+$ blood cells, wherein the T$_{reg}$ cell suppresses T cell proliferation. The method of the present invention comprises isolating a population of mononuclear cells from a human umbilical cord blood sample, contacting the population of mononuclear cells with an antibody that specifically binds CD25 under conditions suitable for formation of a mononuclear cell-antibody complex, and substantially separating the mononuclear cell-antibody complex from said population of mononuclear cells, thereby isolating a regulatory T cell from a population of phenotypically CD45RA$^+$ blood cells. In one embodiment of the invention, the population of phenotypically CD45RA$^+$ blood cells is from umbilical cord blood, preferably a human umbilical cord sample.

The present invention further includes a method of multiplying an isolated regulatory T cell comprising culturing the regulatory T cell in a medium comprising an antibody to CD3 and an antibody to CD28. The medium can further comprise IL-2.

The present invention further comprises a method of inhibiting proliferation of a T cell. The method comprises contacting a T cell with a regulatory T cell isolated by the method described herein.

The present invention also includes kit for isolating a regulatory T cell from a human umbilical cord blood sample. The kit comprises an antibody that specifically binds CD25 bound to a physical support, an applicator, and an instructional material for the use thereof.

The present invention also includes kit for multiplying a T$_{reg}$ cell from a human umbilical cord blood sample. The kit comprises an antibody that specifically binds CD3 bound to a physical support, an antibody that specifically binds CD28 bound to a physical support, an applicator, and an instructional material for the use thereof.

The present invention further comprises a regulatory T cell isolated by the methods of the present invention.

BRIEF DESCRIPTION OF THE FIGURES

The foregoing summary, as well as the following detailed description of the invention, will be better understood when read in conjunction with the appended drawings. For the purpose of illustrating the invention, there are depicted in the drawings certain embodiments of the invention. However, the invention is not limited to the precise arrangements and instrumentalities of the embodiments depicted in the drawings. All error bars represent one standard deviation above and below the mean.

FIGS. 1A through 1D, is a series of images depicting FACS analysis for CD45RA and CD45RO expression and optimum purifications of CD45RA$^+$ and CD45RO$^+$ cells.

FIG. 3, comprising

FIG. 4, comprising

FIGS. 6A through 6D, is a series of images depicting that CD4$^+$CD25$^+$ cord blood cells are a distinct population. FIG. 6 comprises representative FACS plots of peripheral blood mononuclear cells (PBMC), cord blood mononuclear cells (CBMC) and purified CD4$^+$CD25$^+$ cells from both sources. FIG. 6 is representative of 10 donors and 10 cell purification experiments. FIG. 6A depicts distinct populations of CD4$^+$ and CD25$^+$ cells in cord blood with a wide separation of CD25$^+$ cells from CD25$^-$ cells. FIG. 6B is an image depicting that CD4$^+$CD25$^+$ cells constitute 1-2% of PBMC, and that a large number of these cells are CD25-dim (arrow). FIG. 6C is an image depicting that CD25$^+$ cells purified from cord blood by direct anti-CD25-microbeads are a purer population. FIG. 6D is an image depicting CD25$^+$ cells purified from adult blood by direct anti-CD25-microbeads.

FIG. 8, comprising FIG. 8A is a graph depicting the kinetic curves of proliferation over a one week MLR. Cord blood derived cells essentially block MLR (●), adult cell lines selected directly by MACS have weak suppressor function (□), and stringently selected adult cells (CD25++lineage-) have moderate potency (■). CD25− cells are not suppressive (*). FIG. 8A is representative of 10 experiments. FIG. 8B is a scatter plot demonstrating the consistency of suppression at day 6 of MLR of cord blood derived (●), versus direct MACS adult cell lines (□), or stringently purified adult lines (CD25++lineage-) (■). FIG. 8C is a graph depicting graded numbers of cultured $T_{reg}$ cells added to an MLR reaction to determine the minimum number needed for potent inhibition. Up to a 1:32 dilution (roughly 1,560 suppressors/50,000 responders) markedly impaired MLR when using cord blood derived suppressor cell lines (■), versus 1:16 for selected potent subset of stringently purified adult lines (pCD25++lin-) (Δ). Two lines each are depicted, representative of 6 adult and cord blood derived suppressor cell lines. FIG. 8D is a graph depicting the maturation of dendritic cells (DC) prior to MLR, by lipopolysaccharide (LPS) or TNF/polyIC combination. Inclusion of these stimulating factors in MLR fails to bypass suppression. FIG. 8D is representative of 3 experiments.

FIG. 9, comprising FIG. 9A is a graph depicting an impairment in the accumulation of cytokines produced by activated T cells, specifically IL-2, IFN-gamma, GM-CSF, TNF-alpha, IL-5, and IL-10 is observed. No alteration in TGF-beta 1 accumulation is detectable. FIG. 9A depicts IL-2 levels on day 2, and other cytokines on day 6, the respective times of peak of accumulation in control MLR cultures. FIG. 9B is a graph depicting minimal alteration of chemokine levels at early timepoints (Day 2), and modest decreases in levels at late time-points (Day 7) for rantes, IL-8, and MIP-1a. FIG. 9 is representative of 4 MLR experiments.

FIG. 10, comprising FIG. 10A is an image demonstrating that CD25 and intracellular CTLA4 expression remains high on cord blood T cells, expression is lower in adult derived T cells, and expression largely returns to baseline for the CD25-derived cell lines. FIG. 10B is an image depicting that CD62L and CD27 expression remains uniformly high on cord blood T cell lines, also on a subset of the adult lines, and diminishes on the CD25-derived cell lines. FIG. 10 is representative of 10 cell lines each, analyzed at 4 weeks of culture.

FIG. 11, comprising FIG. 11A is a graph depicting levels of FoxP3 mRNA assessed by real time PCR analysis. Samples are freshly isolated cells (fresh CD25), cell lines after 4 weeks of culture (Cx CD25), and 4 week cultured cell lines 24 hours after re-stimulation with anti-CD3/CD28 beads (Restim CD25), as indicated. Data are plotted as fold comparison to mRNA levels present in freshly isolated CD8+ T cells (CD8). FIG. 11B is a series of images of a western blot analysis of FoxP3 protein expression in cells cultured for 4 weeks and restimulated with anti-CD3/CD28 beads for the time indicated. Histone H3 was used as a loading control for nuclear proteins. FIG. 11 is representative of 4 independent experiments.

FIG. 12, comprising FIG. 12A is a graph depicting cell lines reactivated with anti-CD3/CD28 beads. FIG. 12B is a graph depicting CD25− and CD25+ cells reactivated with PMA/ionomycin. FIG. 12C is an image depicting expression of CD69, OX40(CD 134), and GITR intact. FIG. 12D is an image depicting that cell surface LAP expression is specific for CD25+ derived cell lines. Resting cell lines were negative for these activation antigens prior to re-stimulation.

FIG. 13, comprising FIG. 13A is a graph depicting that antibodies to immunosuppressive factors IL-10 and TGF beta, as well as anti-IL10R, or combinations of all three fail to reverse suppression mediated by cultured $T_{reg}$ cell lines. FIG. 13B is a graph depicting that antibodies to negative signaling molecules, CTLA4 and PD1, do not reverse suppression. FIG. 13C is an image depicting the lack of suppression from antibodies to GITR or GITR-L. Agonist antibodies to OX40 partially reverse suppression while antibody to OX40L partially enhances suppression. FIG. 13D is a graph depicting that multiple TGF-beta neutralizing antibodies and soluble receptors do not prevent suppressor cell effector function. FIGS. 13A through C are representative of 6 independent experiments, FIG. 13D is representative of 3 independent experiments.

DETAILED DESCRIPTION OF CERTAIN EMBODIMENTS OF THE INVENTION

Figure 1:
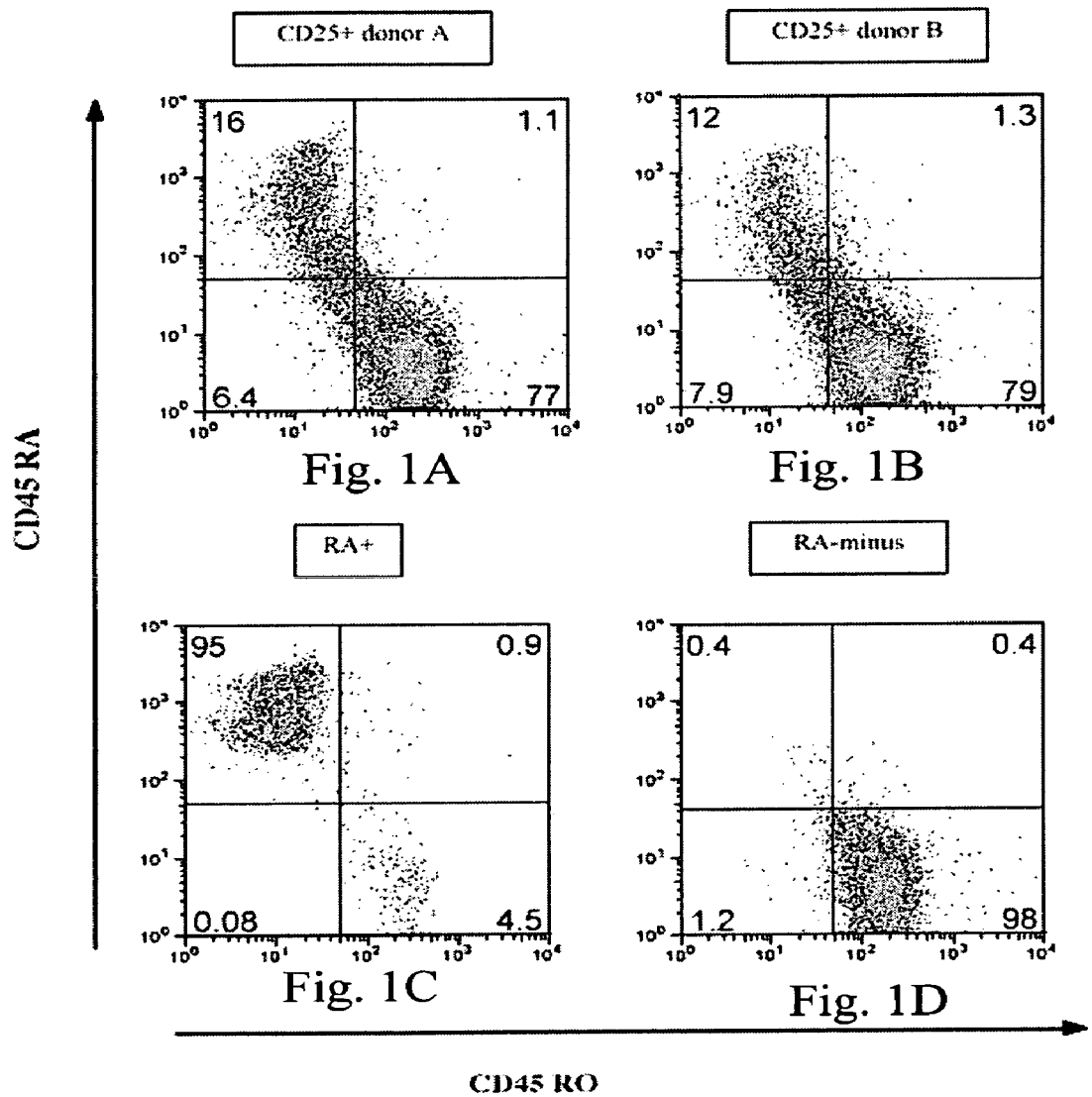
FIG. 1, comprising

The present invention encompasses methods and kits for the isolation and expansion of an enhanced population of T regulatory cells ($T_{reg}$) having the CD45RA+ phenotype. The term "enhanced", as used herein refers to at least 20% more, preferably 30%, preferably 40%, even more preferably 50%, even more preferably about 60%, even more preferably 60%, even more preferably 70%, even more preferably 80%, even more preferably 90%, and even more preferably 100% more than an object that is not enhanced. As an example, an enhanced population of regulatory cells has at least 20% more regulatory cells than a population that is not enhanced. The preferred source of such cells was found to be human umbilical cord blood. Methods for producing large numbers of active, potent suppressor $T_{reg}$ cells from other sources, such as adult human blood, have been confounded by the presence of memory T cells expressing CD25 at low to moderate levels (CD25dim cells), and conventional activated T-cells (CD25+) that interfere with $T_{reg}$ cell purification. The term "$T_{reg}$" is used herein to refer to a regulatory T cell that expresses both CD4 (CD4+) and CD25 (CD25+). However, as demonstrated by the data disclosed herein, both of these types of T cells (memory and activated) are generally lacking, or in lower numbers, in umbilical cord blood. This is because, as disclosed herein, cord blood cells develop in a protected environment and are immunologically naïve. Therefore, the present invention demonstrates that the CD25+ $T_{reg}$ cells in umbilical cord blood are more readily purified than those derived from other sources, such as human adult peripheral blood.

A cell that is "CD25+" or that "expresses CD25" is contrasted herein to a cell that is CD25− or does not express a detectable level of CD25. A cell that is "CD25dim," as used herein has a lower detectable level of CD25 expression than a CD25+ cell or a "CD25bright" cell. In addition, culturing and multiplying these cells is facilitated and simplified because feeder cells are not necessary to expand $T_{reg}$ cell populations.

T$_{reg}$ cells are critical to self and allograft tolerance in mice. Studies of human T$_{reg}$ have been hindered by low numbers present in peripheral blood and difficult purification. The data disclosed herein demonstrate that cord blood is a superior source for T$_{reg}$ isolation and cell line generation compared to adult blood. Cord blood CD4$^+$CD25$^+$ cells were purified, and cell lines were generated that consistently exhibited potent suppressor activity, with >95% suppression of allogeneic MLR (29/30 donors). Cultured T$_{reg}$ cells blocked cytokine accumulation in MLR, with inhibition of chemokine production. These cell lines uniformly expressed CD25, CD62L, CCR7, CD27, and intracellular CTLA4. Further, FoxP3 protein, but not mRNA, was specifically expressed. Upon re-stimulation with anti-CD3/CD28 beads, the cultured T$_{reg}$ produced minimal cytokines (IL-2, IFN-gamma, and IL-10), and preferentially expressed TGF-beta latency associated protein. Cytokine production however, was restored to normal levels by re-stimulation with PMA/ionomycin. Cord blood derived cultured suppressor cell function was predominantly independent of IL-10 and TGF-beta. The data disclosed herein demonstrate that cord blood contains a significant number of T$_{reg}$ precursor cells, capable of potent suppressor function after culture activation. Banked cord blood specimens may serve as a readily available source of T$_{reg}$ for immunotherapy.

The present invention further encompasses T$_{reg}$ cells isolated from human umbilical cord blood samples that have more potent suppressor activity and cytokine suppression capabilities than those derived from other sources. In marked contrast to the prior art, the data disclosed herein demonstrates that T$_{reg}$ cells isolated from human umbilical cord blood have a potent ability to suppress T cell proliferation and to suppress T cell activation-dependent cytokines. Further, the present data further demonstrates that cord blood CD4$^+$CD25$^+$ cells can form potent suppressor cells after isolation and culture. The present invention encompasses a method for purifying T$_{reg}$ cells using a straightforward direct antibody-based purification system for isolating such suppressor cells. After activation and multiplication with anti-CD3/CD28 beads and culture in IL-2, cord blood derived CD4$^+$CD25$^+$ cells acquire potent suppressor function, which was maintained for long periods of time. Thus, the present invention further encompasses a method for inhibiting T cell proliferation and a method for inhibiting cytokine production.

To date, all assays of suppressor cell phenotype and function reveal that the cord blood derived, and the purest of the adult derived cells, have similar profiles. Flow cytometric analysis, cytokine production potential, and functional profiling have all been essentially the same. Thus, the data disclosed herein indicate that both types of lines, when pure, express equivalent suppressor mechanisms and potency, and the advantage of cord blood primarily relates to ease of purification and culture.

The availability of large numbers of suppressor cells has enabled the biochemical and molecular characterization of these special cells. Using the methods disclosed herein, greater than 300 million uniform and potent suppressor cells can be generated from one average sized research grade cord blood unit (~300 million cells) without a cell sorter. These results demonstrate a 1% CD4$^+$CD25$^+$ cell recovery, and a 100-fold expansion in culture. This number of cells enables further characterization of TCR signaling alterations, FoxP3 regulation and function, and suppressor effector mechanisms. In addition, an important utility of these cells is to enable clinical testing of a new form of immunotherapy. Suppressor cell lines can be useful for enhancing allograft tolerance induction or down-modulating autoimmune diseases.

The present invention comprises a method of isolating a T$_{reg}$ cell from an umbilical cord blood sample. The articles "a" and "an" are used herein to refer to one or to more than one (i.e., to at least one) of the grammatical object of the article. By way of example, "a T$_{reg}$ cell" means one T$_{reg}$ cell or more than one T$_{reg}$ cell. The T$_{reg}$ cell isolated using the methods of the present invention, as demonstrated by the data disclosed herein, inhibits T cell proliferation. The method of the present invention comprises isolating a population of cord blood mononuclear cells from an umbilical cord blood sample. A "population" is used herein to refer to a group of cells having a substantially similar phenotypic characteristic, such as being mononuclear cells, or expressing CD25RA. Methods for isolating mononuclear cells from a biological sample, such as a cord blood sample, are well known in the art, and include, but art not limited to, using a density gradient centrifugation techniques so that blood components, such as plasma and erythrocytes, are separated from mononuclear cells. Methods for isolating mononuclear cells from a blood sample include the Ficoll-Hypaque technique.

The cord blood mononuclear cells so isolated can be depleted of cells expressing certain antigens, including, but not limited to, CD34, CD8, CD14, CD19 and CD56. Depletion of these cells can be accomplished using an isolated antibody, a biological sample comprising an antibody, such as ascites, an antibody bound to a physical support, and a cell bound antibody. The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, *Using Antibodies: A Laboratory Manual*, Cold Spring Harbor Laboratory Press, NY; Harlow et al., 1989, *Antibodies: A Laboratory Manual*, Cold Spring Harbor, New York; Houston et al., 1988, *Proc. Natl. Acad. Sci. USA* 85:5879-5883; Bird et al., 1988, *Science* 242:423-426). By the term "specifically binds," as used herein, is meant a compound, e.g., a protein, a nucleic acid, an antibody, and the like, which recognizes and binds a specific molecule, but does not substantially recognize or bind other molecules in a sample.

The antibody of the present invention can be bound to a physical support, such as a magnetic bead, a dynal bead, a microbead, a column, an adsorption column, and an adsorption membrane. Conjugating an antibody to a physical support is well known in the art. Id. Alternatively, an antibody conjugated to a physical support, such as a magnetic bead, can be purchased from a variety of sources, such as Milteny Biotec (Auburn, Calif.).

A variety of antibodies are useful in the present invention. As will be understood by one skilled in the art, any antibody that can recognize and bind to a CD antigen of interest, such as CD25, CD4, CD34, CD8, CD14, CD19 and CD56 is useful in the present invention. Methods of making an using such antibodies are well known in the art. For example, polyclonal antibodies useful in the present invention are generated by immunizing rabbits according to standard immunological techniques well-known in the art (see, e.g., Harlow et al., 1988, supra). Such techniques include immunizing an animal with a chimeric protein comprising a portion of another protein such as a maltose binding protein or glutathione (GSH) tag polypeptide portion, and/or a moiety such that the marker protein is rendered immunogenic (e.g., a marker protein conjugated with keyhole limpet hemocyanin, KLH) and a portion comprising the respective marker protein amino acid residues. The chimeric proteins are produced by cloning the appropriate nucleic acids encoding the marker protein into a plasmid vector suitable for this purpose, such as but not limited to, pMAL-2 or pCMX.

However, the invention should not be construed as being limited solely to methods and compositions including these antibodies or to these portions of the protein antigens. Rather, the invention should be construed to include other antibodies, as that term is defined elsewhere herein, to $T_{reg}$ cell surface marker proteins, or portions thereof. Further, the present invention should be construed to encompass antibodies, inter alia, bind to the $T_{reg}$ proteins and they are able to bind the protein present on Western blots, in solution in enzyme linked immunoassays, in FACS assays, in magnetic-activated cell sorting (MACS) assays, and in immunofluorescence microscopy.

One skilled in the art would appreciate, based upon the disclosure provided herein, that the antibody can specifically bind with any portion of the marker protein and the full-length protein can be used to generate antibodies specific therefor. However, the present invention is not limited to using the full-length protein as an immunogen. Rather, the present invention includes using an immunogenic portion of the protein to produce an antibody that specifically binds with a specific $T_{reg}$ cell surface protein. That is, the invention includes immunizing an animal using an immunogenic portion, or antigenic determinant, of the cell surface marker protein.

The antibodies can be produced by immunizing an animal such as, but not limited to, a rabbit, a mouse or a goat, with a protein of the invention, or a portion thereof, by immunizing an animal using a protein comprising at least a portion of an $T_{reg}$ cell surface antigen, or a fusion protein including a tag polypeptide portion comprising, for example, a maltose binding protein tag polypeptide portion, covalently linked with a portion comprising the appropriate amino acid residues. One skilled in the art would appreciate, based upon the disclosure provided herein, that smaller fragments of these proteins can also be used to produce antibodies that specifically bind an $T_{reg}$ cell surface protein.

The invention encompasses polyclonal, monoclonal, synthetic antibodies, and the like. The present invention further comprises the use of biologically active fragments of antibodies, such as an Fab fragment, an F(ab')$_2$ fragment, an Fv fragment and an scFv fragment of an antibody. One skilled in the art would understand, based upon the disclosure provided herein, that the crucial feature of the antibody of the invention is that the antibody bind specifically with an $T_{reg}$ cell surface protein. That is, the antibody of the invention recognizes an $T_{reg}$ cell or a fragment thereof (e.g., an immunogenic portion or antigenic determinant thereof), on Western blots, in immunostaining of cells, or immunoprecipitates the protein using standard methods well-known in the art.

One skilled in the art would appreciate, based upon the disclosure provided herein, that the antibodies can be used to immunoprecipitate and/or immuno-affinity purify their cognate antigen as described in detail elsewhere herein, and additionally, by using methods well-known in the art. In addition, the antibody can be used to isolate a $T_{reg}$ in a population of cord blood mononuclear cells derived from an umbilical cord blood sample. Thus, by using an antibody to a $T_{reg}$ cell surface marker, such as CD25, a $T_{reg}$ can be identified, enriched or isolated. One skilled in the art would understand, based upon the disclosure provided herein, that any marker, either native or genetically engineered, expressed on an $T_{reg}$ cell surface, is thus useful in the present invention.

The skilled artisan would appreciate, based upon the disclosure provided herein, that present invention includes use of either a single antibody recognizing a single $T_{reg}$ antigen but that the invention is not limited to use of a single antibody. Instead, the invention encompasses use of at least one antibody where the antibodies can be directed to the same or different $T_{reg}$ antigens.

The generation of polyclonal antibodies is accomplished by inoculating the desired animal with the antigen and isolating antibodies which specifically bind the antigen therefrom using standard antibody production methods such as those described in, for example, Harlow et al. (1988, supra).

Monoclonal antibodies directed against full length or peptide fragments of a protein or peptide may be prepared using any well known monoclonal antibody preparation procedures, such as those described, for example, in Harlow et al. (1988, Id.) and in Tuszynski et al. (1988, *Blood,* 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, *Critical Rev. Immunol.* 12:125-168), and the references cited therein. Further, the antibody of the invention may be "humanized" using the technology described in, for example, Wright et al., id., and in the references cited therein, and in Gu et al. (1997, *Thrombosis and Hematocyst,* 77:755-759), and other methods of humanizing antibodies well-known in the art or to be developed.

Once expressed, whole antibodies, dimers derived therefrom, individual light and heavy chains, or other forms of antibodies can be purified according to standard procedures known in the art.

In one embodiment of the invention, a phasge antibody library may be generated. To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al., supra.

Bacteriophage which encode the desired antibody, may be engineered such that the protein is displayed on the surface thereof in such a manner that it is available for binding to its corresponding binding protein, e.g., the antigen against which the antibody is directed, such as an $T_{reg}$ cell surface antigen. Thus, when bacteriophage which express a specific antibody are incubated in the presence of a cell which expresses the corresponding antigen, the bacteriophage will bind to the cell. Bacteriophage which do not express the antibody will not bind to the cell.

The antibodies used in the present invention are placed in contact with the population of cord blood mononuclear cells isolated from a human umbilical cord sample under conditions suitable for formation of a cord blood mononuclear cell-antibody complex. That is, the method of the present invention comprises contacting a population of cord blood mononuclear cells with an antibody that specifically binds to a $T_{reg}$ cell in the population of cord blood mononuclear cells so that the antibody binds to an antigen, including CD25, on the $T_{reg}$ cell. "Conditions suitable" is used herein to refer to temperature, pH, buffers, time, and other factors that facilitate the binding of an antibody to its cognate antigen or to a cell, such as a $T_{reg}$ cell. Conditions that are suitable for an antibody binding to an antigen or to a cell, or to an antigen on a cell, are well known in the art and are usually from about 4° C. to about 20° C. to about 37° C. for a period of time from about 2 minutes to about 5 minutes to about 30 minutes to about 1 hour to about 24 hours. Various buffers are well known in the art and include, for example, Tris, phosphate buffered saline, and the like. Various examples of conditions suitable for the formation of a cord blood mononuclear cell-antibody complex are described in, for example, Harlow et al., 1988, supra.

The present invention further comprises the step of substantially separating the cord blood mononuclear cell-antibody complex from a population of cord blood mononuclear cells. That is, as demonstrated by the data disclosed herein, the present method of isolating a $T_{reg}$ cell that inhibits T cell proliferation from an umbilical cord blood sample comprises substantially separating such a $T_{reg}$ cell from other cord blood mononuclear cells in a sample. As the term is used herein, "substantially separated from" or "substantially separating" refers to the characteristic of a population of first substances being removed from the proximity of a population of second substances, wherein the population of first substances is not necessarily devoid of the second substance, and the population of second substances is not necessarily devoid of the first substance. However, a population of first substances that is "substantially separated from" a population of second substances has a measurably lower content of second substances as compared to the non-separated mixture of first and second substances.

Various techniques may be employed to separate a $T_{reg}$ bound to an antibody, such as an anti-CD25 antibody, from cells that do not have an antibody bound cell surface marker by removing antibody-bound $T_{reg}$ cells from the cell mixture of cord blood mononuclear cells. Alternatively, various techniques may be employed to separate the $T_{reg}$ containing an antibody-bound cell surface marker from cells that do not have an antibody bound cell surface marker by removing from the cell mixture $T_{reg}$ not bound by an antibody.

In one embodiment, the CD25 cell surface marker is used to separate antibody-bound $T_{reg}$ from T cells and other cord blood mononuclear cells not conjugated with antibody. In one aspect of the invention, the antibodies may be attached to a solid support to allow for crude separation. The separation techniques employed should maximize the retention of viability of the fraction to be collected. For "relatively crude" separations, that is, separations where up to 10%, usually not more than about 5%, preferably not more than about 1%, of the total cells present having the marker, may remain with the cell population to be retained, various techniques of different efficacy may be employed. The particular technique employed will depend upon efficiency of separation, cytotoxicity of the methodology, ease and speed of performance, and necessity for sophisticated equipment and/or technical skill, all of which is within the ability of the ordinary skilled artisan.

Procedures for separation may include magnetic separation, using antibody-coated magnetic beads or dynal beads, affinity chromatography, cytotoxic agents joined to a monoclonal antibody or used in conjunction with a monoclonal antibody, e.g., complement and cytotoxins, and "panning" with antibody attached to a solid matrix, e.g., plate, or other convenient technique. Techniques providing accurate separation include fluorescence activated cell sorters, which can have varying degrees of sophistication, e.g., a plurality of color channels, low angle and obtuse light scattering detecting channels, impedance channels, etc., as well as magnetic activated cell sorters.

Conveniently, the antibodies may be conjugated with markers, such as magnetic beads, which allow for direct separation, biotin, which can be removed with avidin or streptavidin bound to a support, fluorochromes, such as FITC, which can be used with a fluorescence activated cell sorter, or the like, to allow for ease of separation of the particular cell type. Any technique may be employed which is not unduly detrimental to the viability of the remaining cells. Other techniques include, but are not limited to, dense particles for density centrifugation, an adsorption column, an adsorption membrane, and the like.

In one embodiment of the invention, an antibody specific for an cord blood derived cell surface marker is conjugated to a magnetic bead. A population of cord blood derived mononuclear cells is contacted with the magnetic bead-antibody conjugate, under conditions suitable for binding of the antibody conjugate to an $T_{reg}$ cell surface antigen, such as CD25, displaying the antigen. After incubation under conditions suitable for binding, such as, but not limited to, an incubation at 4° C. for 20 minutes, a $T_{reg}$ positive for the antigen are selected by passing the entire sample through a magnetic-based separation apparatus. Upon evacuation or elution of free solution from the apparatus, only the magnetically-retained marker-containing cells will remain. The antigen-containing $T_{reg}$ cells are then eluted from the apparatus, resulting in an enriched, isolated or purified population of $T_{reg}$ cells. In one aspect of the invention, a $T_{reg}$ marker is CD25.

After substantial isolation of the cells lacking comprising a $T_{reg}$ antigen, such as CD25, generally by at least about 50%, preferably at least about 70%, even more preferably about 80%, even more preferably about 90% or greater than 90%, the cells can be separated by a fluorescence activated cell sorter or other methodology having high specificity, such as magnetic activated cell sorting (MACS). Multi-color analyses can be employed with the FACS which is particularly convenient.

In order to increase the stringency of the of the present method of isolating a $T_{reg}$ cell from a human umbilical cord blood sample, a $T_{reg}$ cell that have been substantially separated from a population of cord blood mononuclear cells can be contacted again with an antibody that specifically binds CD25 under conditions suitable for formation of a cord blood mononuclear cell-antibody complex followed by substantially separating the cord blood mononuclear cell-antibody complex from the population of cord blood mononuclear cells. This step can be performed one or more times to isolate a human $T_{reg}$ cell from an umbilical cord blood sample.

The present invention further comprises a method of multiplying, expanding or otherwise culturing a $T_{reg}$ cell isolated using the methods disclosed herein. As demonstrated by the data disclosed herein, multiplying a $T_{reg}$ cell isolated by the methods of the present invention can by multiplied by about 100 fold using the methods disclosed herein. Following isolation, a $T_{reg}$ cell is incubated in cell medium in a culture apparatus for a period of time or until the cells reach confluency before passing the cells to another culture apparatus. The culturing apparatus can be of any culture apparatus commonly used in culturing cells in vitro. Preferably, the level of confluence is greater than 70% before passing the cells to another culture apparatus. More preferably, the level of confluence is greater than 90%. A period of time can be any time suitable for the culture of cells in vitro. $T_{reg}$ cell medium may be replaced during the culture of the $T_{reg}$ cells at any time. Preferably, the $T_{reg}$ cell medium is replaced every 3 to 4 days. $T_{reg}$ cells are then harvested from the culture apparatus whereupon the $T_{reg}$ cells can be used immediately or cryopreserved to be stored for use at a later time. $T_{reg}$ cells may be harvested by trypsinization, EDTA treatment, or any other procedure used to harvest cells from a culture apparatus.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

The medium used to multiply the $T_{reg}$ cells of the present invention comprises an antibody to CD3, and antibody to CD28, and a cytokine, preferably, but not limited to, IL-2. This is because, as demonstrated by the data disclosed herein, a cell isolated by the methods of the present invention can be multiplied approximately 100 fold by culturing the cell with an antibody that binds CD3, and antibody that binds CD28, and IL-2. Further, as also disclosed herein, cells multiplied using the methods of the present invention are uniform and potent suppressor cells. Further, since the $T_{reg}$ cells of the present invention are immunologically naïve, such cells can be administered to an animal, preferably a mammal, even more preferably a human, to suppress an immune reaction, such as those common to autoimmune diseases such as diabetes, psoriasis, rheumatoid arthritis, multiple sclerosis, GVHD, enhancing allograft tolerance induction, transplant rejection, and the like. In addition, the cells of the present invention can be used for the treatment of any condition in which a diminished or otherwise inhibited immune response, especially a cell-mediated immune response, is desirable to treat or alleviate the disease.

The CD3 antibody and CD28 antibody used in the methods of the present invention can be any of the antibodies known in the art, those disclosed elsewhere herein, or those yet to be discovered. Further, and preferably, the antibodies of the present invention are conjugated or otherwise attached to a bead, such as a magnetic bead or a dynal bead. Such beads are known in the art and are described elsewhere herein.

The medium of the present invention further comprises a cytokine, preferably IL-2. This is because, as demonstrated by the data disclosed herein, the addition of IL-2 to the medium used in the methods of the present invention results in an approximate 100 fold expansion of the $T_{reg}$ cells of the present invention. IL-2 and other cytokines are well known in the art and are available commercially from various sources.

The $T_{reg}$ of the present invention further comprises certain antigenic markers, some of which are present when a $T_{reg}$ cell is isolated from an umbilical cord blood sample, some of which are present when the $T_{reg}$ cell is multiplied, cultured, or otherwise expanded according to the methods of the present invention. Such antigenic markers are useful in the identification of a $T_{reg}$ cell of the present invention, and allow one of skill in the art to determine if a $T_{reg}$ cell isolated and multiplied according to the methods of the present invention has the properties and biological activities of a $T_{reg}$ cell of the present invention. Such biological activities include, but are not limited to, suppression of an allogeneic immune response, inhibition of cytokine accumulation in an immune response accompanied by less inhibition of chemokine production, the production of IL-2, IL-10 and gamma interferon, the expression of TGF-beta latency associated protein (LAP), and suppressor activity independent of IL-10 and TGF-beta. Markers on the $T_{reg}$ cell of the present invention include, but are not limited to, CD25, CD4, CTLA4, CD27, CD26L and Fox P3.

The present invention further comprises a method for inhibiting proliferation of a T cell. Such inhibition can occur in vitro or in vivo, preferably in an animal, more preferably in a mammal, even more preferably in a human. This is because, as demonstrated by the data disclosed herein, HLA mismatched T cells in a mixed lymphocyte reaction (MLR) were inhibited from proliferating by a factor greater than about 95% in the presence of a $T_{reg}$ cell isolated and multiplied according to the methods of the present invention. Further, as demonstrated by the data disclosed herein, $T_{reg}$ cells isolated and/or multiplied according to the methods of the present invention are potent suppressors of T cell proliferation at ratios of from about 1:16 to about 1:32 ($T_{reg}$:T cell). Further, the $T_{reg}$ cells of the present invention are active in suppressing an immune response when a antigen presenting cell, such as a dendritic cell, is mature and activated. Thus, the cells of the present invention can be used to inhibit active immune responses or to prevent an immune response.

The method of the present invention comprises contacting a T cell with a $T_{reg}$ cell isolated and/or expanded according to the methods of the present invention such that the proliferation of a T cell is inhibited. The $T_{reg}$ cell can be administered using techniques well known in that art so that a $T_{reg}$ contacts, or is in proximity, to an immune cell, such as a T cell, dendritic cell, plasma cell, and the like.

The method of inhibiting the proliferation of a T cell using a $T_{reg}$ isolated and/or cultured according to the methods of the present invention encompasses the preparation and use of pharmaceutical compositions comprising a $T_{reg}$ of the invention as an active ingredient. Such a pharmaceutical composition may consist of the active ingredient alone, as a combination of at least one active ingredient (e.g., an effective dose of an $T_{reg}$) in a form suitable for administration to a subject, or the pharmaceutical composition may comprise the active ingredient and one or more pharmaceutically acceptable carriers, one or more additional (active and/or inactive) ingredients, or some combination of these.

As used herein, the term "pharmaceutically acceptable carrier" means a chemical composition with which the active ingredient may be combined and which, following the combination, can be used to administer the active ingredient to a subject.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs, birds including commercially relevant birds such as chickens, ducks, geese, and turkeys, fish including farm-raised fish and aquarium fish, and crustaceans such as farm-raised shellfish.

Pharmaceutical compositions that are useful in the methods of the invention may be prepared, packaged, or sold in formulations suitable for oral, rectal, vaginal, parenteral, topical, pulmonary, intranasal, intra-lesional, buccal, ophthalmic, intravenous, intra-organ or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers and other immune inhibitory compounds, such as cyclosporine, steroids, antibodies to pro-inflammatory cytokines, inhibitory cytokines, such as IL-10, and the like.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

The $T_{reg}$ of the invention and/or a $T_{reg}$ expanded using the methods of the present invention, can be administered to an animal, preferably a human. When the $T_{reg}$ of the invention are administered, the amount of cells administered can range from about 100,000 cells to about 300 billion cells wherein the cells are infused into the animal, preferably, a human patient in need thereof. While the precise dosage administered will vary depending upon any number of factors, including but not limited to, the type of animal and type of disease state being treated, the age of the animal and the route of administration.

The $T_{reg}$ may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

An $T_{reg}$ may be co-administered with the various other compounds (cytokines, chemotherapeutic drugs, immunosuppressive drugs, among many others). Alternatively, the compound(s) may be administered an hour, a day, a week, a month, or even more, in advance of the $T_{reg}$, or any permutation thereof. Further, the compound(s) may be administered an hour, a day, a week, or even more, after administration of a $T_{reg}$, or any permutation thereof. The frequency and administration regimen will be readily apparent to the skilled artisan and will depend upon any number of factors such as, but not limited to, the type and severity of the disease being treated, the age and health status of the animal, the identity of the compound or compounds being administered, the route of administration of the various compounds and the $T_{reg}$, and the like.

Further, it would be appreciated by one skilled in the art, based upon the disclosure provided herein, that where the $T_{reg}$ is to be administered to a mammal, the cells can be treated so that they are in a "state of no growth"; that is, the cells are incapable of dividing when administered to a mammal. As disclosed elsewhere herein, the cells can be irradiated to render them incapable of growth or division once administered into a mammal. Other methods, including haptenization (e.g., using dinitrophenyl and other compounds), are known in the art for rendering cells to be administered, especially to a human, incapable of growth.

The invention includes various kits which comprise the reagents used to isolate a $T_{reg}$ from a human umbilical cord blood sample. The kit comprises an antibody that specifically binds to a molecule on the surface of a $T_{reg}$ cell, such as CD25, an applicator, and instructional materials which describe use of the kit to perform the methods of the invention. Although exemplary kits are described below, the contents of other useful kits will be apparent to the skilled artisan in light of the present disclosure. Each of these kits is included within the invention. By the term "applicator," as the term is used herein, is meant any device including, but not limited to, a hypodermic syringe, a pipette, and the like, for administering the compounds and compositions of the invention.

"Instructional material," as that term is used herein, includes a publication, a recording, a diagram, or any other medium of expression which can be used to communicate the usefulness of the composition and/or compound of the invention in the kit for effecting alleviating or treating the various diseases or disorders recited herein. Optionally, or alternately, the instructional material may describe one or more methods of alleviating the diseases or disorders in a cell or a tissue or a mammal, including as disclosed elsewhere herein.

The invention further includes a kit for multiplying a $T_{reg}$ from a human umbilical cord blood sample. The kit comprises an antibody that specifically binds to CD3 and an antibody that specifically binds to CD28. The antibodies of the present kit can be isolated antibodies, antibodies bound to a physical support, such as a magnetic bead, or other antibodies described elsewhere herein or known in the art. The kit can further comprise a cytokine, such as IL-2, for culturing, multiplying or otherwise expanding a $T_{reg}$ of the present invention. The kit is used pursuant to the methods disclosed in the invention. The kit can further comprise an applicator and an instructional material for the use thereof.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLES

Example 1

Isolation and Culture of CD45RA$^+$ Cells From Adult Human Peripheral Blood

MACS Purification of CD25$^+$ and CD25$^-$ Cells for Culture

Peripheral blood mononuclear cells (PBMC) were isolated from buffy coat preparations, which were derived from the whole blood of normal healthy volunteer donors (Memorial Blood Centers, Minneapolis, Minn.). Leukocyte rich buffy coat cells were centrifuged over Ficoll-Hypaque layers to collect PBMC. CD25$^+$ cells were isolated using the following indirect antibody based microbeads. PBMC were stained with anti-CD25-FITC, clone 2A3 (Becton Dickinson Immunocytometry Systems, San Jose, Calif.), washed and then bound secondarily to anti-FITC multi-sort microbeads (5 microliters/$10^7$ cells, Miltenyi Biotec, Auburn, Calif.) and positively selected. The CD25$^+$ cells were reapplied to a second column, washed and re-eluted. After column purification, the anti-FITC multisort beads were detached. The CD25$^+$ cells were further depleted of CD8, CD 14, CD19, CD20, and CD56 expressing cells with a cocktail of mAb-coated microbeads for lineage depletion. These CD25$^+$ lineage depleted cells (DC-8x-minus) were then selected for CD45RA by direct positive selection with anti-CD45RA microbeads (20 microliters/$10^7$ cells, Miltenyi). In some cases, a further purification of anti-HLA-DR+ cells was isolated from the CD45RA$^-$ cells by positive selection with anti-HLA-DR microbeads (20 microliters/$10^7$ cells, Miltenyi). The CD25$^-$ cells were further depleted of CD25 by a second round of depletion with direct anti-CD25 microbeads (20 microliters/$10^7$ cells, Miltenyi). After CD25 depletion these cells were then positively selected for CD4 with direct anti-CD4 microbeads (20 microliters/$10^7$ cells, Miltenyi).

Culture of CD25$^+$ and CD25$^-$ Cells

Isolated CD25$^+$ cells, CD25$^+$ subsets, or CD4$^+$CD25$^-$ control cells were cultured at 1 million total cells/ml in 24 well plates. An equal number of irradiated CD4$^+$CD25$^-$ feeder cells were added to the cultures. Anti-CD3/CD28 mAb-coated dynabeads (University of Pennsylvania, Philadelphia, Pa.) were added at a 3:1 bead to cell ratio as a growth stimulus, and moderate dose IL-2 was added on day 3, at 50 IU/ml in the fresh media (Chiron, Emeryville, Calif.) (Godfrey, et. al., 2004, Blood, 104: 453-461; Levine, et al., 1998, J. Hemather., 7: 437-48). For cord blood cultures, feeder cells were not required for culture or preservation of suppressor function, and therefore were not used. Cell cultures were split as needed, approximately 1/3 every 3 days during the fast growth phase. Culture media was RPMI-1640 (Invitrogen-Gibco, Carlsbad, Calif.) supplemented with 10% FCS (Invitrogen-Gibco), and L-glutamine, penicillin, and streptomycin.

Cell lines previously isolated using a MACS based strategy for isolation of CD4$^+$CD25$^+$ cells for $T_{reg}$ cell line generation from adult blood exhibited variable potency, which was possibly caused by contaminating conventional T cells. To improve on the purification strategy, CD25$^+$ cells were analyzed for subsets by flow cytometric analysis. A subset of CD4+CD25+ cells could be further enriched for suppressor cells, or conversely, a subset might be enriched for conventional T cells. The approach described herein was to characterize subset markers, selectively purify these cell subsets, and then evaluate their ability to form cell lines with potent suppressor function.

The first markers analyzed were CD45RO, a marker of memory cells, and CD45RA, a marker of naive T cells. The CD45RO+ subset of CD4+CD25+ cells has been reported to contain the suppressor cells, as freshly isolated CD4+CD25+ CD45RO+ cells contained most of the suppressor activity of CD4+CD25+ cells (Jonuleit, et al., 2001, *J. Exp. Med.*, 193: 1285-1294). CD4+CD25+CD45RO-minus cells had minimal suppressor activity in functional assays (secondary allogeneic MLR). The CD4+CD25+CD45RO-minus cells were suggested to be conventional T cells. As conventional T cells typically overgrow suppressor cells in culture, depletion of the CD4+CD25+CD45RO-minus cells was investigated as a means to improve cell line generation.

Figure 2:
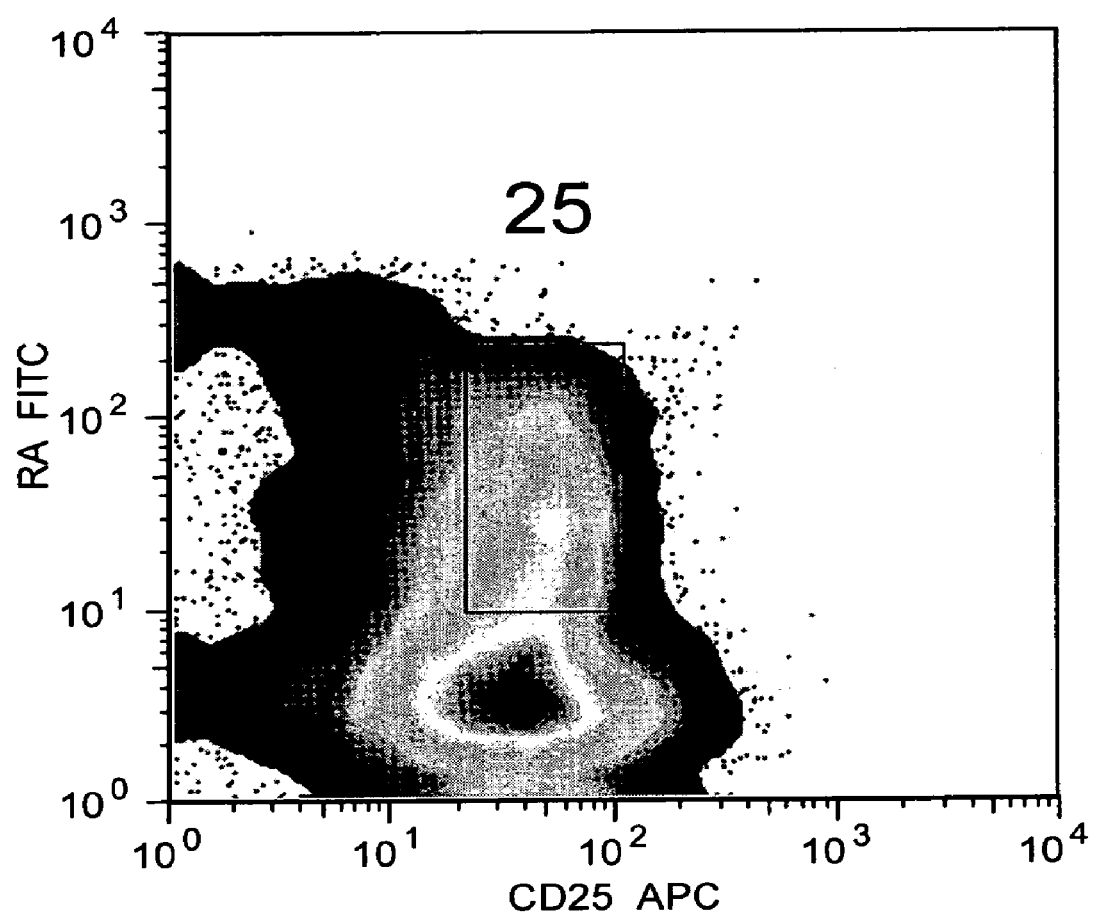
FIG. 2 is an image depicting that CD45RA$^+$ cells do not express CD25 at even the highest levels, and that CD25 bright cells do not detectably express CD45RA.

Purified CD4+CD25+ cells were assessed for CD45RA and CD45RO expression by FACS analysis (FIG. 1). The CD25+ cells coexpressed CD45RO on approximately 80% the cells (mean 80%, range 62-89, n=6). The CD25+ cells also contained a subset of cells which coexpressed CD45RA on approximately 20% of cells (mean 24%, range 15-38, n=6). High level expression of these antigens was mutually exclusive, but there are a significant number of double positive cells only expressing low amounts of both antigens, and a two-color dot-plot reveals a whole spectrum of expression. The CD45RA+ cells did not express CD25 at the highest levels, and the CD25 bright cells, thought to be the true $T_{reg}$ cells, appear to not express CD45RA (FIG. 2). These data therefore indicate that depletion of the CD45RA subset would further enrich for the CD45RO+ $T_{reg}$ cells, and elimination of these CD4+CD25+CD45RA+ cells was attempted.

The indirect purification system with a cleavable microbead allowed purification of CD25+ cells, removal of the magnetic bead, and then depletion of the CD45RA+ cells. Using a typical buffy coat, the starting material was approximately 500 million cells, and through purification obtain approximately 10 million CD25+ cells, 7 million CD25+ lineage-negative cells, 5 million CD45RA-minus cells, and 1 million CD45RA+ cells were derived. Purifications from two donors are depicted (FIG. 1). These various CD25+ populations were cultured with one round of stimulation with anti-CD3/28 beads. After 3 weeks, the cell lines were tested for ability to suppress allo MLR.

To evaluate suppressor function of these cell lines, an HLA-mismatched allo-MLR assay was used as a functional readout. The CD4+ responder and DC stimulated MLR assays are very robust and consistent amongst donors, and therefore served as our standard measure of suppression. All cell lines were initially screened for suppressor activity in MLR after 2-3 weeks of culture, and then further analyzed over the next 3-4 weeks.

Figure 3A:
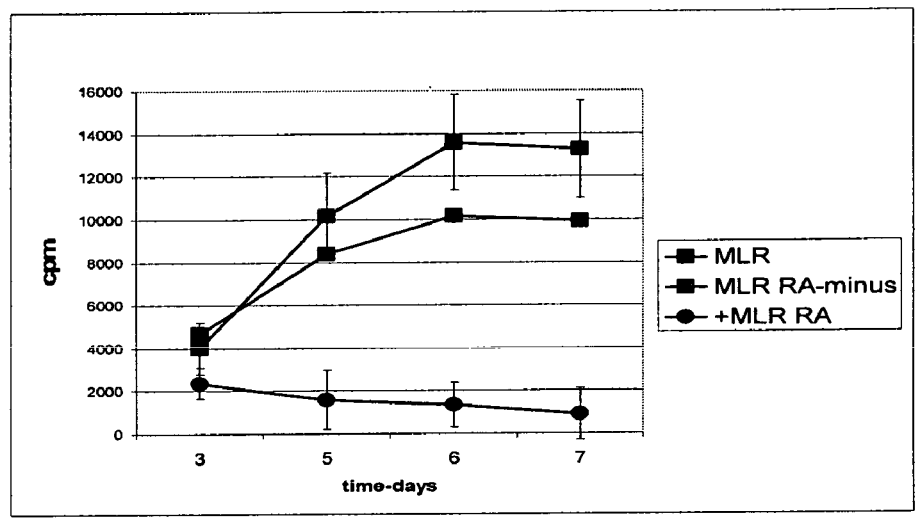
FIGS. 3A and 3B, is a series of images depicting potent suppressor activity in CD45RA$^+$ cells as measured by a mixed lymphocyte reaction.
Figure 3B:
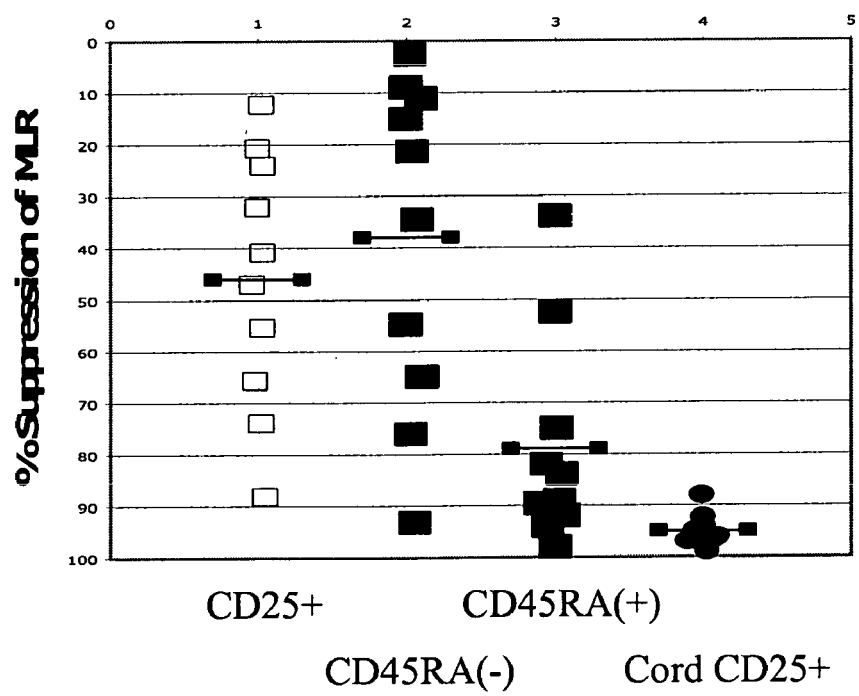

Surprisingly, it was the CD45RA+ derived cell lines (which were expected to be conventional T cells and lack activity), that demonstrated potent suppressor activity (FIG. 11). In contrast, the CD45RA-minus cell derived lines had very poor suppressor function. Twelve cell line donors were tested, and 10/12 RA cell lines demonstrated potent suppressor activity and 2/12 RA-minus lines demonstrated similar activity. These data, and the percent suppression mediated by these cell lines is depicted in a scatter plot, which also includes straight CD25+ selected cells from adult blood and cord blood (FIG. 3).

Two Main Subsets of Human CD25+ Cells, CD45RA+ and HLA-DR+

Figure 4A:
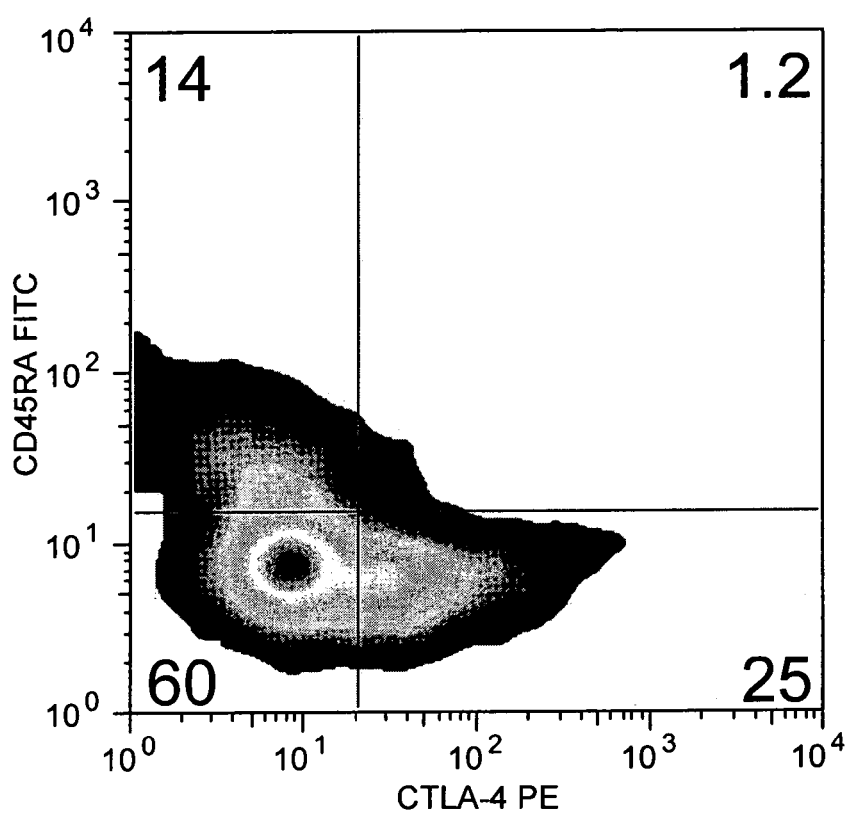
FIGS. 4A through 4D, is a series of images depicting that CD45RA cells are CTLA-4 negative (FIG. 4A) and HLA-DR$^-$ (FIG. 4B). CD25$^+$ bright cells are HLA-DR$^+$ (FIG. 4C) and they double stain for intracellular CTLA-4 (FIG. 4D), thus depicting two distinct cell subsets.
Figure 4B:
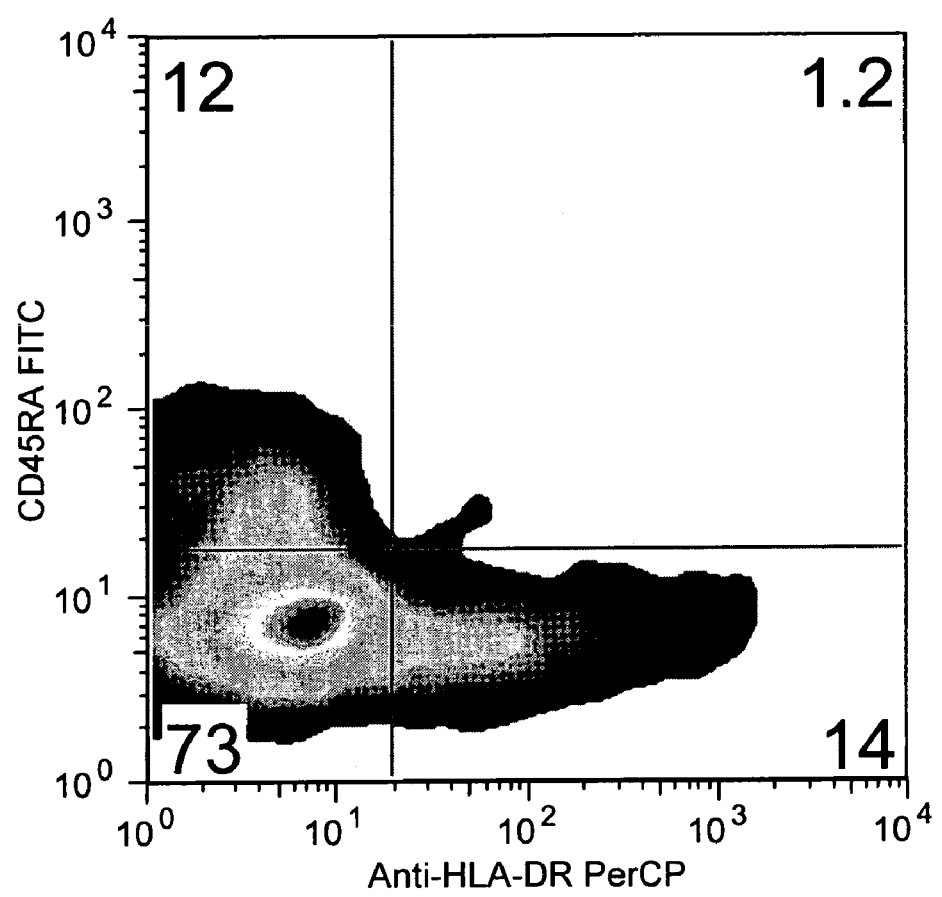
Figure 4C:
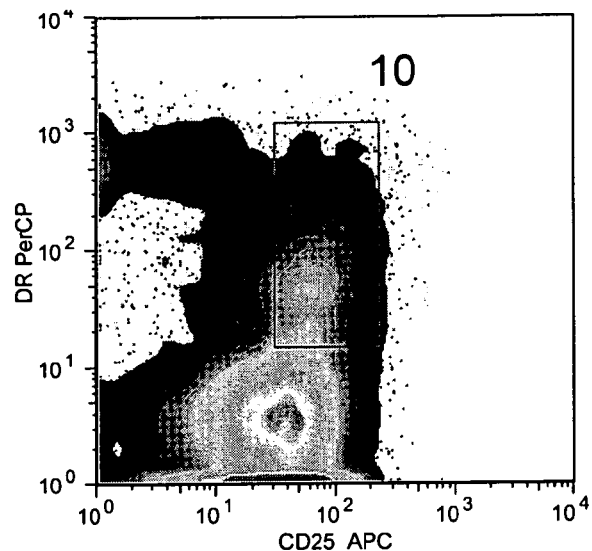
Figure 4D:
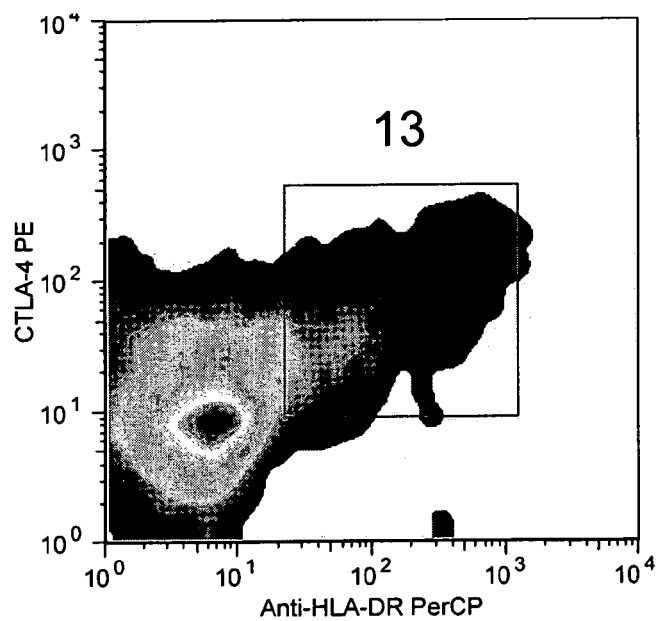

Further analysis of CD25+ cell subsets revealed that the CD45RA+ cells were distinct from the CD25+ bright, classically described human $T_{reg}$ cell (Baecher-Allan, et al., 2001, *J. Immunol.*, 167: 1245-1253; Godfrey, et. al., 2004, Blood 104: 453-461; Hoffmann, et al., 2004, *Blood* 104: 895-903). Prior reports have noted these cells to be CD25+ hi, and CTLA-4 positive (Jonuleit, et al., 2001, *J. Exp. Med.*, 193: 1285-1294). The data disclosed herein demonstrate that the CD45RA cells are distinct. In two color dot plots, the CD45RA cells are shown to be intracellular CTLA-4 negative (FIG. 4), HLADR negative (FIG. 4B). Double staining for CD25 verus HLA-DR reveals that the HLA-DR+ cells are the CD25+bright cells (FIG. 4C), and they double stain for intracellular CTLA-4 (FIG. 4D). This demonstrates two distinct cell subsets.

Figure 5:
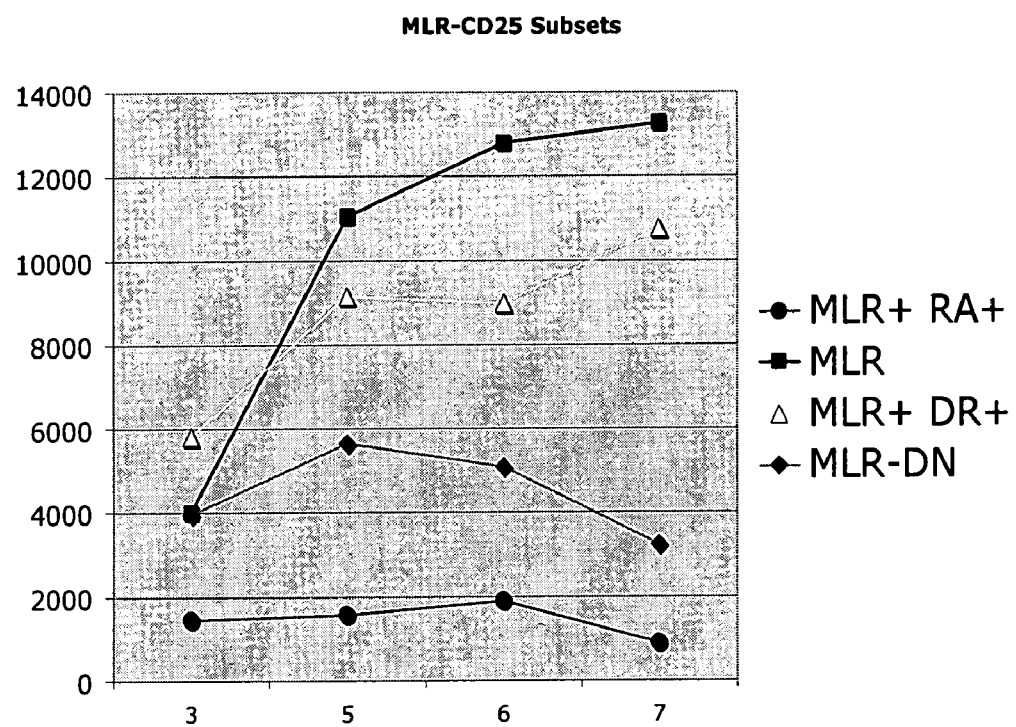
FIG. 5 is a graph depicting the suppressor activity of CD45RA$^+$ cells (RA+), HLA-DR$^+$ cells (DR+) and double negative cells (DN). The most potent suppressor activity is evident in CD45RA$^+$ cells, middle potency in double negative cells and the least potency in HLA-DR$^+$ cells.

Purification of the HLA-DR cells was performed by further positive selection of the CD45RA(-) cell population. This left three subsets of CD25+ cells, the CD45RA+ cells, the HLA-DR+ cells, and the "double negatives". All three subsets were cultured and tested for suppressor function. The CD45RA+ derived cell lines mediated the most potent suppressor function. The double negative cells mediated a middle level of suppression and the HLA-DR+ mediated the worst suppressive activity (FIG. 5).

Example 2

Adult Human CD45RA+ Cells Suppress T-Cell Proliferation

Responder and Stimulator Cells for Mixed Lymphocyte Reaction (MLR) Assay Cultures CD4+CD25− responder T-cells were isolated from buffy coat preparations derived from the whole blood of normal healthy volunteer donors (Memorial Blood Centers, Minneapolis, Minn.). Cells were centrifuged over Ficoll-Hypaque to collect PBMC. PBMC were first depleted of CD25+ cells with anti-CD25 mAb-coated microbeads (Miltenyi-Biotec), before CD4+ T-cells were isolated by positive selection with anti-CD4 mAb-coated magnetic microbeads (Miltenyi-Biotec). Cells were routinely 96-98% pure by FACS analysis. Immature dendritic cells (DC) were generated from CD14+ monocytes (Sallusto and Lanzavecchia, 1994, J. Exp. Med., 179: 1109-1118), isolated from PBMC, by magnetic bead based purification (Miltenyi-Biotec), and were cultured in X-vivo-15 (BioWhittaker, Walkersville, Md.) media at 1 million cells/ml supplemented with GM-CSF (50 ng/ml final) and IL-4 (20 ng/ml final; R&D Systems, Minneapolis, Minn.). Cells were cultured for 5-10 days before use as stimulators in MLR. For some experiments, DC were matured with LPS (Sigma, St. Louis, Mo.) (100 ng/ml), or TNF-alpha (20 ng/ml final) and Poly I:C, a Toll-like receptor (TLR)-3 agonist ligand (20 µg/ml final) (Sigma) for two days (Godfrey, et al., 2004, *Blood* 103: 1158-1165; Cella, et al., 1999, *J. Exp. Med.*, 189: 821-829). DC stimulators were irradiated at 30 Gy.

MLR Assay Culture $5 \times 10^4$ responding CD4+CD25− T-cells and $5 \times 10^3$ DC stimulator antigen presenting cells (APC) were cultured per well in 96 well U-bottom plates. Cultured suppressor or conventional T-cell lines were added at $2.5 \times 10^4$ per well for standard assays, or in graded numbers for titration experiments. For antibody blocking experiments, $10^4$, or $5 \times 10^3$ suppressor cells were used. Culture media was RPMI-1640 supplemented with 10% FCS. Wells were pulsed on days 3, 5, 6, and 7 with $^3$H-thymidine for the last 16 hours of culture.

Each timepoint had 6 replicates. Results expressed in counts per minute. Data was collected with a direct beta counter (no liquid scintillation), thus the magnitude of the results was lower but proportionally correct.

Cytokine Analysis

MLR culture supernatants were spun free of cells and aliquots were frozen at −80° C. For re-stimulations, anti-CD3/CD28 beads were used at a 1:1 bead to cell ratio. Supernatants were evaluated by the Luminex assay system with a latex bead-based multianalyte system (R&D Systems, Minneapolis, Minn.).

Potency of Suppression Mediated by CD45RA$^+$ Derived Cell Lines

Titration experiments were performed to further evaluate suppression potency. Lowering the number of suppressors added to standard DC stimulated MLR cultures demonstrated that nearly full inhibitory activity of cord blood derived suppressors was maintained out to a ratio of 1:16 or 1:32 (as few as 1500 suppressors to 50,000 responders). This is slightly more potent (~2-fold) than the selected most potent adult derived cell lines (CD25$^+$lineage$^-$).

As a further assessment of potency, suppressor cell lines were evaluated in MLR where the DC stimulators had been matured. Activation/maturation of DC with lipo-polysaccharide (LPS), (TLR4 ligand), or the combination of TNF/polyIC (double stranded RNA analog-TLR 3 ligand), did not lead to bypass of suppression. In addition, inclusion of LPS or TNF/Poly IC in the MLR culture, also did not bypass suppression. Thus the CD45RA$^+$ derived T$_{reg}$ cells were both potent and activated DC, which abundantly express costimulatory molecules and cytokines. Further, DC and the expressed costimulatory molecules were not able to bypass the suppressive effect of the CD4$^+$CD25$^+$ cells.

CD45RA$^+$ Derived Suppressor Cells Impair Cytokine Production in MLR

To determine the effects of the suppressor cell lines on responder T cells in MLR assays, the culture supernatants were evaluated for the presence and magnitude of multiple cytokines. Suppressor cell addition to MLR assays markedly reduced accumulation of T cell activation dependent cytokines, including IL-2, IFN-gamma, GM-CSF, TNF-α, and IL-10. Activation dependent cytokine accumulation was minimal at all timepoints during the suppressed MLR. These data demonstrate a marked impairment of T cell activation.

Reactivation of Suppressor Cell Lines Induces Minimal Cytokine Production

To determine the functional capabilities of the suppressive versus conventional T-cell lines we evaluated their potential for cytokine production and cell surface molecule expression after re-stimulation. Cell lines were re-stimulated with anti-CD3/CD28 beads for potent reactivation, and supernatants harvested at defined timepoints for analysis of cytokine content by luminex bead based assay. The CD45RA$^+$ derived cell lines produced essentially no IL-2, IFN-γ, or IL-10, while control CD25$^-$ derived cell lines produced high levels of these cytokines. The accumulation of TNF, GM-CSF, and IL-5, and the chemokine IL-8, was also markedly reduced as compared to control cell lines.

Example 3

Isolation and Culture of Human Cord Blood Having a CD45RA$^+$ Phenotype

The critical role of T$_{reg}$ cells in cord blood immunology and transplantation has not been generally appreciated (Barker, et al., 2003, *Crit. Rev. Oncol. Hematol.*, 48: 35-43). Many researchers use total CD4$^+$ selected cord blood populations as a representative model of truly naïve T cells for purposes of immunological characterization (Kaminski, et al., 2003, *Blood* 102: 4608-4617). However, in light of the data disclosed herein, some prior studies may need to be re-evaluated with CD25 depleted CD4$^+$ cells (Jonuleit, et al., 2000, *J. Exp. Med.*, 192: 1213-1222). These cells may be a contributing factor to the low rate of GVHD experienced in cord blood transplantation (CBT) (Wadlow, et al., 2002, *Biol. Blood. Marrow. Transplant.*, 8: 637-647).

MACS Purification of CD25$^+$ and CD25$^-$CD4$^+$ T-Cells

CD25$^+$ and CD25-CD4$^+$ T-cells were isolated from umbilical cord blood (Red Cross, Saint Paul, Minn.). Cord blood mononuclear cells were prepared by centrifugation over Ficoll-Hypaque according to the manufacturer's directions. After CD34$^+$ depletion with magnetic microbeads (Miltenyi Biotec, Auburn, Calif.), CD25$^+$ cells were isolated by positive selection with directly conjugated anti-CD25 magnetic microbeads (4 microliters per 10$^7$ cells; Miltenyi Biotec). Cells were then applied to a second magnetic column, washed, and re-eluted. After the double column procedure cells were routinely >90% pure (for CD4/CD25) by FACS analysis. The non-CD25 fraction was then applied to another magnetic column to deplete any remaining CD25$^+$ cells, before isolation of CD4$^+$CD25-cells by positive selection with anti-CD4 mAb-coated microbeads (Miltenyi Biotec). Stringent purification of adult CD25$^+$ cells used anti-CD25-FITC and anti-FITC microbeads (2 microliters per 10$^7$ cells), and passage over magnetic column and elution for two cycles. This was followed by releasing the magnetic beads, and subsequent lineage depletion with anti-CD8, CD14, CD19, and CD56 direct conjugated microbeads (CD4$^+$CD25$^{++}$lin-) as described in Godfrey, et al. (2004, *Blood* 104: 453-461).

Culture of Cord Blood T$_{reg}$ Cells

Isolated CD4$^+$CD25$^+$ cells or control CD4$^+$CD25$^-$ cells were cultured as described in Godfrey, et al. (2004, *Blood* 104: 453-461) with anti-CD3/CD28 mAb-coated dynabeads (obtained from the University of Pennsylvania and described in Levine, et al., 1998, *Hematother.*, 7:437-448) at a three-to-one bead to cell ratio. Cells were cultured at 1 million total cells/ml in 24 well plates. IL-2 was added on day 3 at 50 IU/ml (Chiron, Emeryville, Calif.). In contrast to the prior study, all lines were cultured without feeder cells. For cord blood cultures, the addition of irradiated feeder cells (CD4$^+$CD25$^-$ cells) (Godfrey, et al. 2004, *Blood* 104: 453-461), was neither helpful for expansion, nor preservation of suppressor function, therefore feeders were omitted to simplify the culture protocol. Cell cultures were split as needed, approximately one-to-three every three days during the fast growth phase. Culture media was RPMI-1640 (Invitrogen-Gibco, Carlsbad, Calif.) supplemented with 10% fetal calf serum (FCS; Invitrogen-Gibco), and L-glutamine, penicillin, and streptomycin.

Cord Blood Contains a Distinct Population of CD4$^+$CD25$^+$ Cells

Figure 6:
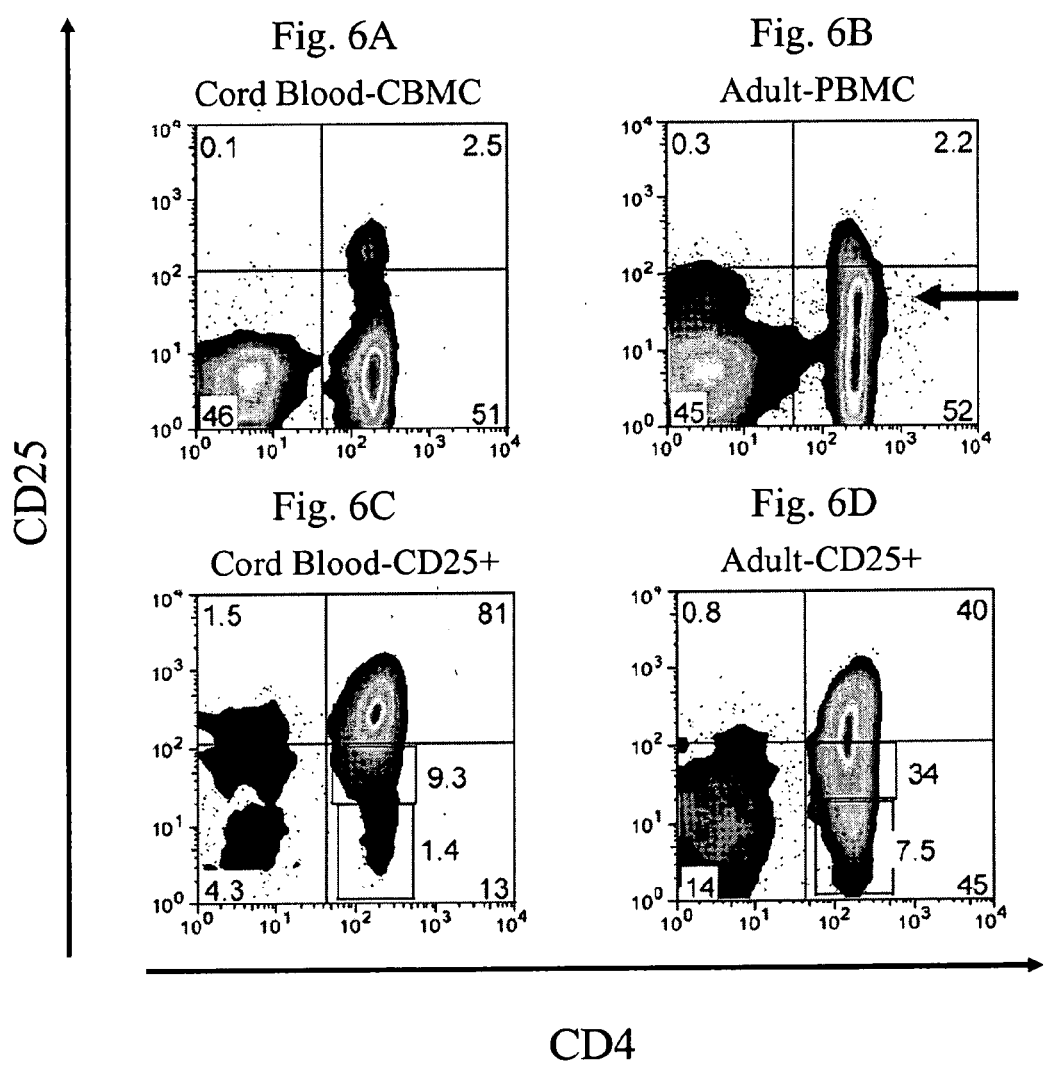
FIG. 6, comprising

Cord blood mononuclear cells (CBMC) have been shown to contain CD4$^+$ T-cells that co-express CD25. Therefore, the present results disclose an evaluation of the potential of these cells for suppressor functions and suppressor cell line generations. FACS analysis was used to confirmed that CBMC contained a significant population of CD4$^+$ T-cells that co-express CD25$^+$, and that this was a discrete population of cells (FIG. 6A). In contrast, adult blood contains CD4$^+$ T-cells with a broad spectrum of levels of CD25, including a large population of non-suppressive CD25-dim cells (FIG. 6B). Approximately 5% of the cord blood CD4$^+$ T-cells distinctly expressed CD25$^+$ (mean 5.2%, range 2.3-9.5%, n=20), a slightly higher percentage than present in adult peripheral blood CD4+ T cells (mean 3.8% of CD4+). For direct comparison of purification, CD25+ $T_{reg}$ cells were isolated from both adult and cord blood using an identical MACS based protocol (direct anti-CD25 based selection). The CD25+ cells purified from cord blood contained a more focused population of CD25+ bright cells (MFI 320 vs 130), and fewer CD25-dim or CD25-negative cells (FIG. 6C), mean 9% (range 5-21%, n=10) and 3% (range 1-9%, n=10) respectively. In comparison, the CD25+ cells derived from adult blood were found to contain more CD25-dim and CD25-negative cells (FIG. 6D), mean 30% (range 25-38%, n=10), and 10% (range 2-24%, n=10) respectively.

Cord Blood CD25+ Cells are CD45RA+

Figure 7:
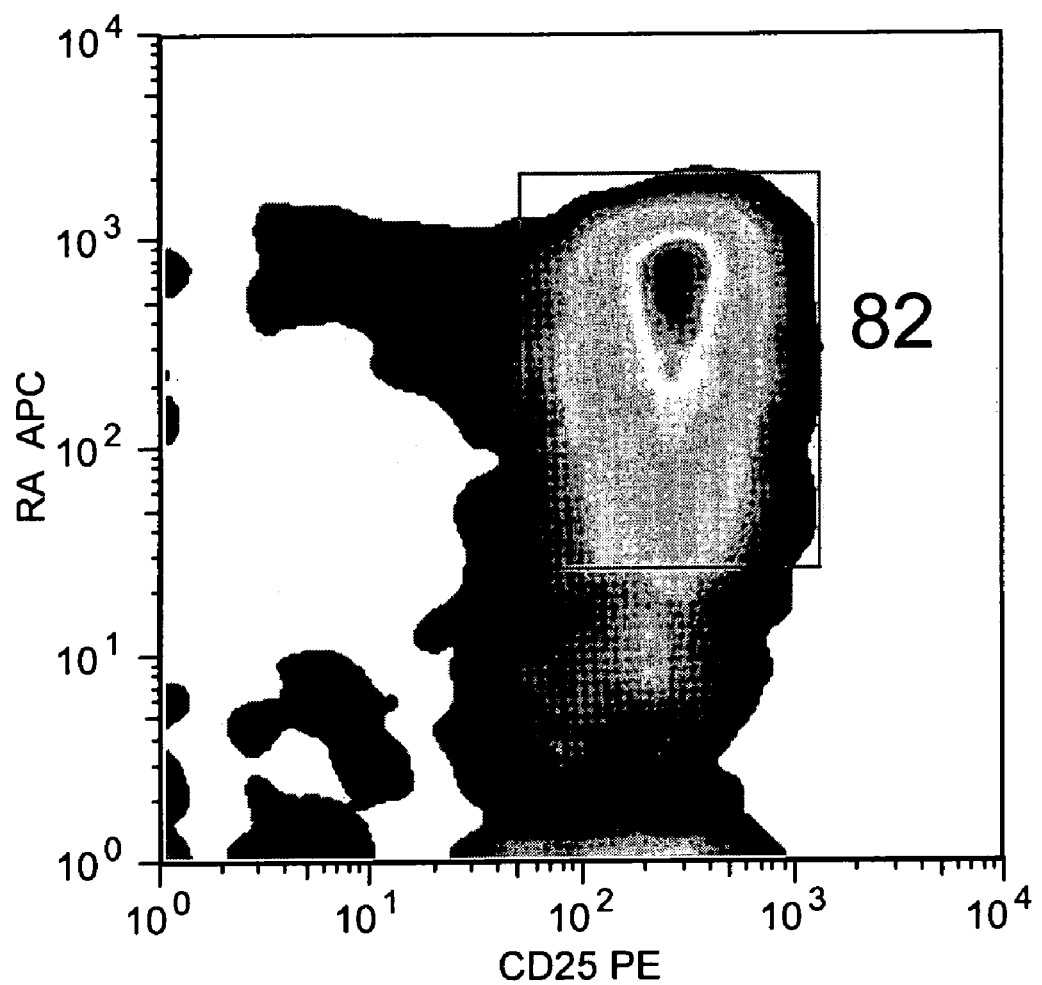
FIG. 7 is an image depicting that cord blood CD25$^+$ cells are CD45RA$^+$ and showing that purified CD25$^+$ cord blood cells are predominantly CD45RA$^+$.

Cord blood CD25+ cells were purified by direct selection. They were stained for CD25 and CD45RA. The cells are predominantly CD45RA+ (FIG. 7).

MACS Selected Cord Blood CD4+CD25+ Derived Cell Lines Consistently Have Potent Suppressor Function Stimulating stringently purified adult derived CD25+ $T_{reg}$ cells with anti-CD3/CD28 coated beads, supplemented with IL-2, induces significant expansion. This culture strategy was used to generate cell lines from purified adult or cord blood CD4+CD25+ cells, as well as cord blood CD4+CD25− cells for comparison. The cord blood derived CD4+CD25+ cells expanded readily in culture; approximately 100 fold over three weeks with a single initial stimulation. After three to four weeks the cell lines stopped expanding in number, and were maintained in IL-2. Thus, the growth curves of these cell lines were similar to that of the adult blood derived CD4+CD25+ cell lines.

Example 4

CD45RA+ Cord Blood Cells Suppress T-Cell Proliferation

Responder and Stimulator Cells for Mixed Lymphocyte Reaction (MLR) Cultures

CD4+CD25− responder T-cells were isolated from buffy coat preparations derived from the whole blood of normal healthy volunteer donors (Memorial Blood Centers, Minneapolis, Minn.). Cells were centrifuged over Ficoll-Hypaque to collect PBMC. PBMC were first depleted of CD25+ cells with anti-CD25 mAb-coated microbeads (Miltenyi-Biotec), before CD4+ T-cells were isolated by positive selection with anti-CD4 mAb-coated magnetic microbeads (Miltenyi-Biotec). Cells were routinely 96-98% pure by FACS analysis. Immature dendritic cells (DC) were generated from CD14+ monocytes (Sallusto, et al., 1994, *J. Exp. Med.*, 179: 1109-1118), isolated from PBMC, by magnetic bead based purification (Miltenyi-Biotec), and were cultured in X-vivo-15 (BioWhittaker, Walkersville, Md.) media at 1 million cells/ml supplemented with GM-CSF (50 ng/ml final) and IL-4 (20 ng/ml final) (R&D Systems, Minneapolis, Minn.). Cells were cultured for 5-10 days before use as stimulators in MLR. For some experiments, DC were matured with LPS (Sigma, St. Louis, Mo.) (100 ng/ml), or TNF-alpha (20 ng/ml final) and Poly I:C, a Toll-like receptor (TLR)-3 agonist ligand (20 μg/ml final) (Sigma) for two days (Spisek, et al., 2001, *Cancer Immunol. Immunother.*, 50: 417-427; Godfrey, et al., 2004, *Blood* 103: 1158-1165). DC stimulators were irradiated at 30 Gy.

MLR Assay Culture $5 \times 10^4$ responding CD4+CD25− T-cells and $5 \times 10^3$ DC stimulator APC were cultured per well in 96 well U-bottom plates. Cultured suppressor or conventional T-cell lines were added at $2.5 \times 10^4$ per well for standard assays, or in graded numbers for titration experiments. For antibody blocking experiments, $10^4$ or $5 \times 10^3$ suppressor cells were used. Culture media was RPMI-1640 supplemented with 10% FCS. Wells were pulsed on days 3, 5, 6, and 7 with $^3$H-thymidine for the last 16 hours of culture. Each time-point had 6 replicates. Results were expressed in counts per minute. Data was collected with a direct beta counter (no liquid scintillation), thus the magnitude of the results was lower but proportionally correct.

Suppressor Function of $T_{reg}$ Cells as Determined by MLR Assay

Figure 8A:
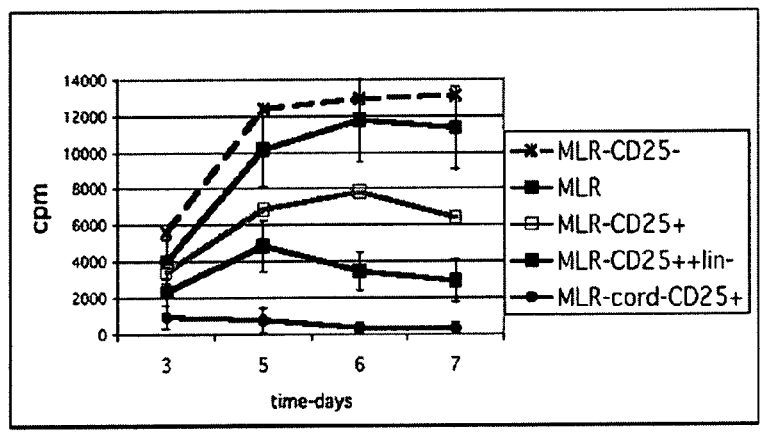
FIGS. 8A through 8D, is a series of images demonstrating that cultured cord blood derived CD4$^+$ CD25$^+$ cells markedly suppress a mixed lymphocyte reaction (MLR) as measured by proliferative inhibition.
Figure 8B:
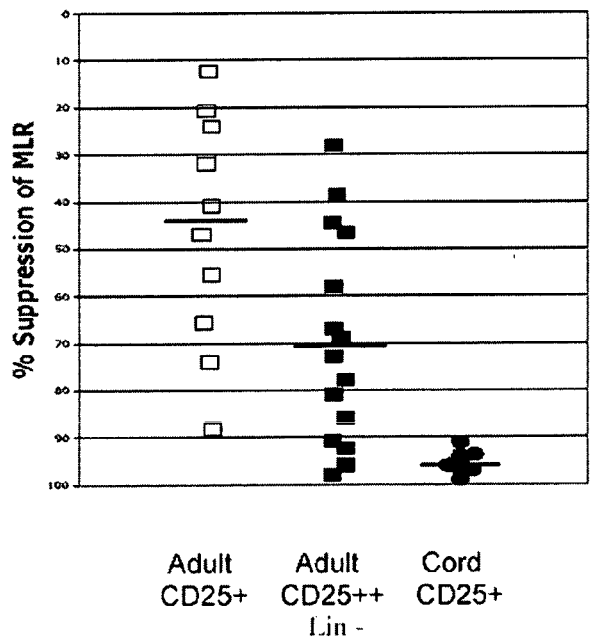
Figure 8C:
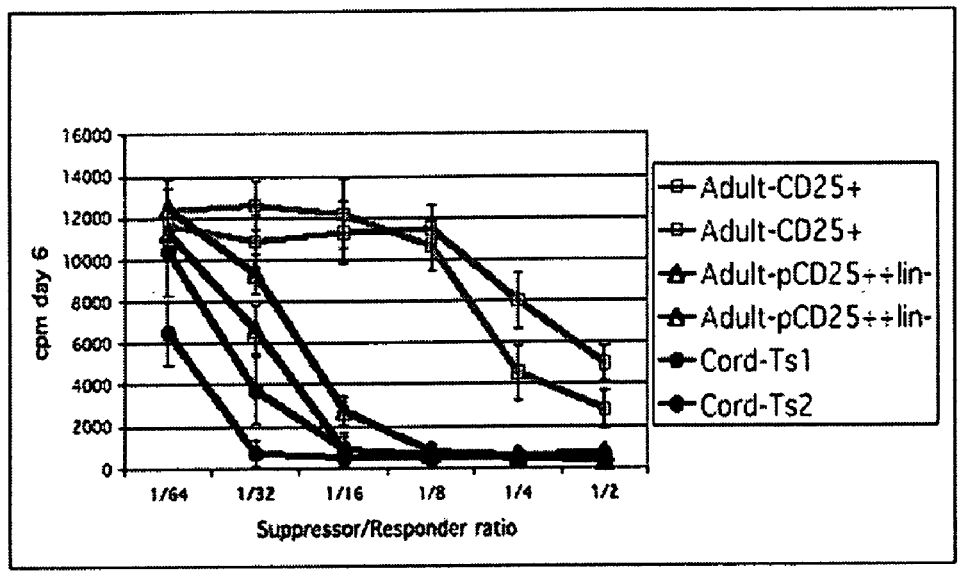
Figure 8D:
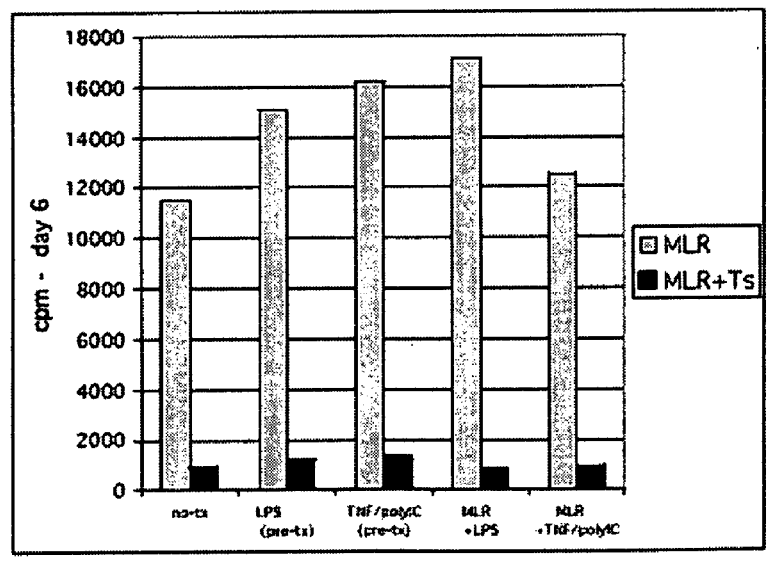

To evaluate suppressor function of the cell lines, an HLA-mismatched allo-MLR assay was used as a functional readout. The CD4+ responder and DC stimulated MLR assays are very robust and consistent amongst donors, and therefore served as the standard measure of suppression. All cell lines were initially screened for suppressor activity in MLR after 2-3 weeks of culture, and then further analyzed over the next 3-4 weeks. Strikingly, the cell lines derived from cord blood CD25+ cells were consistently and potently suppressive (FIG. 8A). Potent suppressive cell lines were isolated from 29 of 30 donors, where inhibition of proliferation was typically >95% (FIG. 8B). Control cell lines derived from adult or cord blood CD25− cells were not suppressive (FIG. 8B). Cell lines derived from adult CD25+ cells (directly isolated), manifested weak and variable suppressive activity (FIGS. 8A and 8B). It was previously reported that stringent MACS based selection was required to generate significant, potent, suppressor cell lines in a subset of adult donors. The suppression mediated by these lines (CD25++lineage) is depicted in FIGS. 8A and 8B, which demonstrates the remarkable consistency of the cord blood derived cell lines.

To further evaluate suppression potency, titration experiments were undertaken. Lowering the number of suppressors added to standard DC stimulated MLR cultures revealed that nearly full inhibitory activity of cord blood derived suppressors was maintained out to a ratio of 1:16 or 1:32 (as few as 1500 suppressors to 50,000 responders). This is more potent (~2-fold) than the selected most potent adult derived cell lines (pCD25+lin-) (FIG. 2C). Cell lines derived from directly selected adult CD25+ cells were poorly suppressive upon titration.

As a further assessment of potency, suppressor cell lines were evaluated in MLR where the DC stimulators had been matured. Activation/maturation of DC with lipopolysaccharide (LPS), (TLR4 ligand), or the combination of TNF/polyIC (double stranded RNA analog-TLR 3 ligand) (Cella, et al., 1999, *J. Exp. Med.*, 189: 821-829), did not bypass suppression (FIG. 2D). In addition, inclusion of LPS or TNF/Poly IC in the MLR culture did not bypass suppression. Thus the cord derived $T_{reg}$ cells were as potent as the best selected adult derived cell lines, and activated DC, which abundantly express co-stimulatory molecules and cytokines, were not able to bypass their suppressive effect.

Figure 9A:
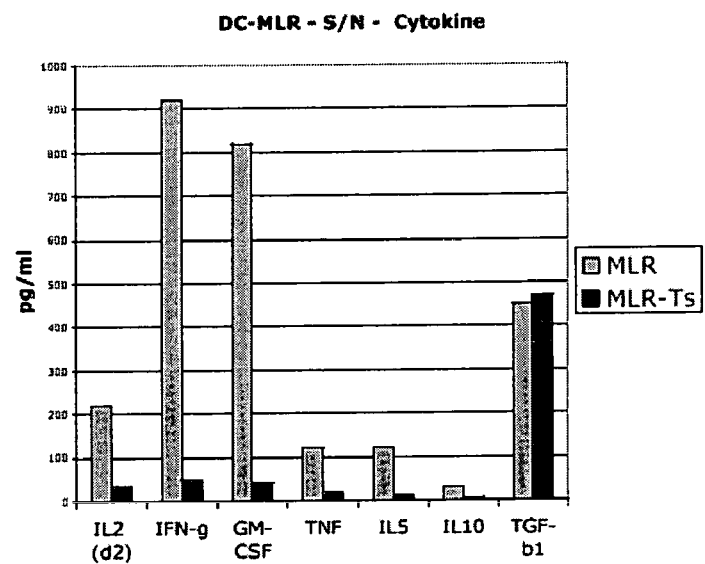
FIGS. 9A through 9B, is a series of images demonstrating that cultured CD4+CD25+ cells markedly suppress cytokine accumulation in MLR, as analyzed by assessment of cytokine levels.
Figure 9B:
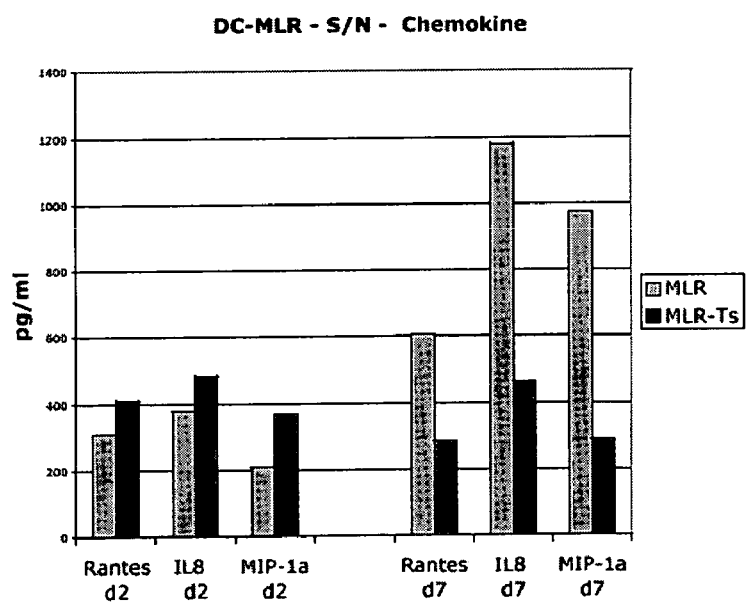

Cord Blood Suppressor Cells Impair Cytokine Production with Less of an Effect on Chemokine Production To determine the effects of the suppressor cell lines on responder T cells in MLR assays, supernatants were evaluated for the presence and magnitude of multiple cytokines. Suppressor cell addition to MLR assays markedly reduced accumulation of T cell activation dependent cytokines, including IL-2, IFN-gamma, GM-CSF, TNF-α, and IL-10. Importantly, levels of TGF-$_{beta-1}$ accumulation did not seem to be altered. Activation dependent cytokine accumulation was minimal at all time-points during the suppressed MLR, with results at time of peak detection in control DC-MLR depicted (FIG. 9A). These data demonstrate a marked impairment of T cell activation. To determine the effects of suppression on selected chemokine expression, MLR supernantants were evaluated for the expression of IL-8 (CXCL8), MIP-1a (CCL3), and RANTES (CCL5), pro-inflammatory chemokines. At early time-points, no effect on accumulation was noted (FIG. 9B). However, at late timepoints in MLR, accumulation was diminished by approximately by 50-75%. Thus, chemokine production appears to be less affected by suppression, and there is some degree of selectivity in the effects of suppressor cells.

Studies of both human and mouse $CD4^+CD25^+$ $T_{reg}$ cells have not revealed a clear mechanism of action of in vitro suppression (Shevach, 2002, *Nat. Rev. Immunol.*, 2: 389-400). Consistent with previous studies, the cord blood derived cultured suppressor cells required cell contact for function (did not suppress across a semi-permeable membrane), and were not cytotoxic. Since TGF beta is variably reported to be a primary factor in $T_{reg}$ mediated suppression (Chen, et al., 2003, *Cytokine Growth Factor Rev.*, 14: 85-89), and rLAP was reported to impair suppressor function (Nakamura, et al., 2004, *J. Immunol.*, 172: 834-842), the TGF-beta pathway was carefully evaluated with multiple neutralizing reagents, including rLAP. Multiple antagonists of TGF-beta, even in various combinations, were found to minimally affect suppression. Neutralizing antibodies to immunosuppressive factor IL-10 or its receptor had no effect on suppression. This is consistent with the lack of IL-10 production by the cord blood suppressor cells even with very strong activating stimuli. Thus, in the presently disclosed in vitro MLR system, neither TGF-beta nor IL-10 appear to be the primary mediators of suppression, and the molecules mediating suppression remain uncharacterized.

Example 5

Characterization of Human Adult $CD25RA^+$ $T_{reg}$ Cells

Monoclonal Antibodies

To evaluate purification, cells were stained with anti-CD25-PE(clone M-A251) (BD Pharmingen, San Diego, Calif.), which is not blocked by anti-CD25-microbeads. Other antibodies for flow cytometry included anti-CD4-PerCP(clone SK3), from (Becton Dickinson Immunocytometry Systems, San Jose, Calif.); anti-CD152-PE(BNI3), anti-CD27-FITC(M-T271), anti-CD62L-APC(Dreg56), anti-CD69-FITC(FN50), anti-CD134(ACT35), from (BD Pharmingen); and anti-GITR-PE(110416), from (R&D Systems). In functional experiments designed for blocking suppression, neutralizing antibodies were used at 10 µg/ml. Antibodies included anti-CTLA4(BNI3) (BD Pharmingen), anti-PD1(J116) (eBioscience, San Diego, Calif.), anti-OX40 (L106) from (Becton Dickinson), and anti-GITR(MAB689), anti-GITR-L(MAB6941), anti-OX40L(MAB10541), anti-IL10(MAB217), anti-IL10-Receptor-alpha(MAB274), anti-TGFbeta-1,2,3(1D11), anti-TGFbeta-1 (MAB1835), polyclonal chicken anti-TGFbeta1/1.2(AF-101-NA), from (R&D Systems).

Cultured Suppressor Cells Function Independent of IL-10 and TGF-Beta

To determine if the cultured suppressor cell lines work through known soluble immunosuppressive or cell surface negative regulatory proteins, DC-MLR suppressor assays were treated with neutralizing or blocking monoclonal antibodies. Assays were evaluated for the reversal of suppression by resumption of proliferation. Initially antibodies to IL-10, IL10R, and TGF-beta$_{1,2,3}$ were tested alone or in various combinations with minimal effect. Only by combining all three antibodies at high doses (30 µg/ml), were modest and probably non-specific reversal of suppression effects seen. Treated control cultures treated with all three antibodies also evidenced increased proliferation, similar to $T_{reg}$ cells treated with all three antibodies.

Flow Cytometry

For immunofluorescence staining, cells were stained for 30 minutes at 4° C. Cells were washed and run on a FACS Calibur cytometer (Becton Dickinson). Data was analyzed by FlowJo software version 4.5 (Treestar, Ashland, Oreg.). Intracellular staining was performed using 2% paraformaldehyde fixed cells, followed by permeabilization and staining in 0.1% saponin containing buffer.

Statistics

All error bars represent one standard deviation above and below the mean.

Phenotype of $CD45RA^+$ Derived Suppressor Lines

Cell lines were analyzed by flow cytometry for antigens associated with suppressor cell phenotype. Suppressor cell lines were cultured in parallel with $CD4^+CD25^-$ derived cell lines which served as conventional T-cell controls. The cell lines maintained a relatively stable phenotype and function for the next 3-5 weeks. The $CD45RA^+$ derived $CD25^+$ cell lines maintain remarkably uniform expression of multiple antigens, including CD25, intracellular CTLA4, CD27 and CD62L. In comparison, the CD45RA(−) derived cell lines, were heterogeneous for these antigens.

The $CD45RA^\pm$ derived $CD25^+$ cell lines maintained high expression of cell surface CD25 and intracellular CTLA4, an expression pattern considered typical of the $T_{reg}$ phenotype. This occurs despite the fact that other activation antigens such as CD69, CD71, and OX40 have returned to baseline expression. The $CD45RA^+$ derived suppressor cell lines also uniformly express both CD62L and CD27. Within potent adult derived suppressor cell lines, the cells with suppressor function reside within this double positive subset (Godfrey, et. al., 2004, Blood 104: 453-461). $CD25^-$ derived cells lines also maintain CD27 expression, but at a lower level than $CD25^+$ derived cell lines. This CD27dim expression pattern was also noted with adult derived $CD25^-$ derived cell lines (Godfrey, et. al., 2004, *Blood* 104: 453-461).

Example 6

Characterization of Human Cord Blood Derived $T_{reg}$ Cells

Real Time PCR

Total RNA was extracted using TRI-reagent (Molecular Research Center, Cincinnati, Ohio) or RNAeasy (Qiagen, Valencia, Calif.). cDNA was synthesized from 1 µg of each RNA sample using Taqman universal master mix (Applied Biosystems, Foster City, Calif.). 10 ng was used in each qPCR reaction. All samples were run in duplicate. Primers and probes for FoxP3 and cyclophillin A were purchased from Applied Biosystems. Real time PCR was performed using the ABI Prism 7900 (Advanced Biosystems). FoxP3 message levels were determined after normalizing data to cyclophillin A.

Western Blotting

Nuclear extracts were prepared according to the manufacturer's directions using Active Motif (Carlsbad, Calif.) and 70 µg of protein were loaded per lane. Samples were run on NuPage 10% Bis-Tris mini-gels (Invitrogen). Proteins were transferred to PVDF membranes and incubated with Goat anti-FoxP3 antibody (AB2481) (Abcam, Cambridge, Mass.), followed by Rabbit anti-Goat IgG horseradish peroxidase. Blots were developed with SuperSignal WestPico Chemiluminescense substrate (Pierce, Rockford, Ill.).

Cytokine Analysis

MLR culture supernatants were spun free of cells and aliquots were frozen at −80° C. For re-stimulations, anti-CD3/CD28 beads were used at a one-to-one bead to cell ratio, or PMA at 2 ng/ml and ionomycin at 500 ng/ml were used. Cells were cultured at 1 million/cells ml media in 24 well plates. Supernatants were evaluated by the Luminex assay system with a latex bead-based multianalyte system (R&D Systems, Minneapolis, Minn.).

Monoclonal Antibodies

To evaluate purification, cells were stained with anti-CD25-PE (clone M-A251) (BD Pharmingen, San Diego, Calif.), which is not blocked by anti-CD25-microbeads. Other antibodies for flow cytometry included anti-CD4-PerCP (clone SK3; Becton Dickinson Immunocytometry Systems, San Jose, Calif.); anti-CD152-PE (BNI3), anti-CD27-FITC (M-T271), anti-CD62L-APC (Dreg56), anti-CD69-FITC (FN50), anti-CD134 (ACT35), from (BD Pharmingen); and anti-GITR-PE (110416), biotinylated anti-LAP (27240) from (R&D Systems). In functional experiments designed for blocking suppression, neutralizing antibodies were used at 10 μg/ml. Antibodies included anti-CTLA4 (BNI3) (BD Pharmingen), anti-PD1 (J116) (eBioscience, San Diego, Calif.), anti-OX40 (L106; Becton Dickinson), and anti-GITR (MAB689), anti-GITR-L (MAB6941), anti-OX40L (MAB 10541), anti-IL10 (MAB217), anti-IL10-Receptor-$_{alpha}$ (MAB274), anti-TGF$_{beta-1,2,3}$ (1D11), anti-TGF$_{beta-1}$ (MAB1835), polyclonal chicken anti-TGF$_{beta1/1.2}$(AF-101-NA), polyclonal goat anti-TGF$_{beta}$RII (AF-241-NA), anti-LAP (MAB246), polyclonal goat anti-LAP (AF-246-NA), recombinant LAP (246-LP), and recombinant TGF-$_{beta}$RII-Ig (1003-RT; R&D Systems).

Flow Cytometry

For immunofluorescence staining, cells were stained for 30 minutes at 4° C. Cells were washed and run on a FACS Calibur cytometer (Becton Dickinson). Data was analyzed by FlowJo software version 4.5 (Treestar, Ashland, Oreg.). Intracellular staining was performed using 2% paraformaldehyde fixed cells, followed by permeabilization and staining in 0.1% saponin containing buffer.

Phenotype and FoxP3 Expression of Cord Blood Derived Suppressor Lines

Figure 10A:
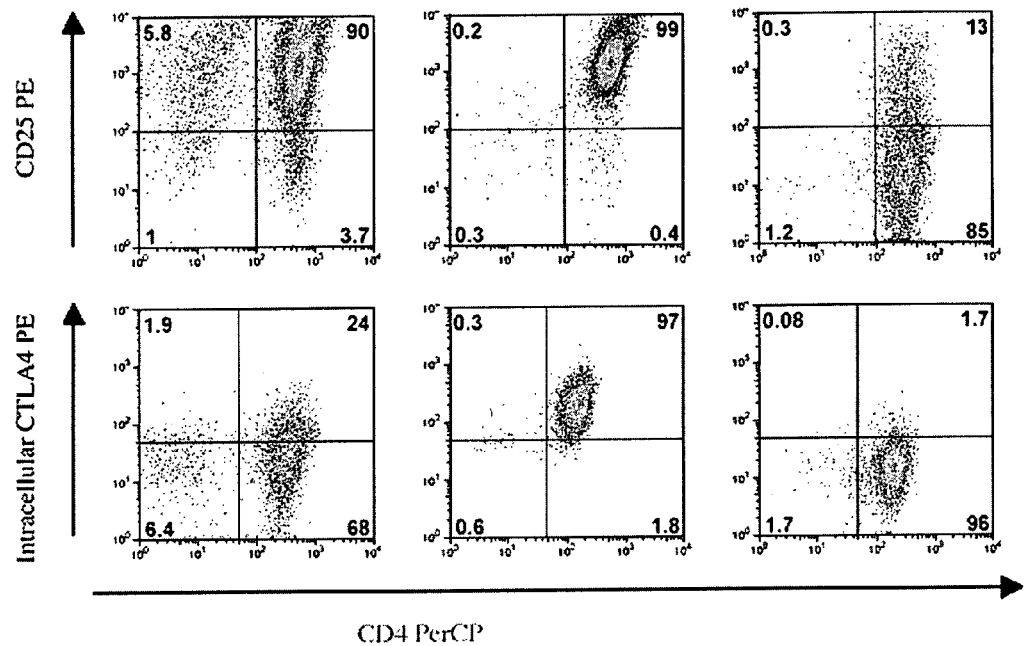
FIGS. 10A and 10B, is an image depicting representative plots of a flow cytometric comparison of CD25+, CD25−, and CD25-derived cell lines after 3-4 weeks culture expansion.
Figure 10B:
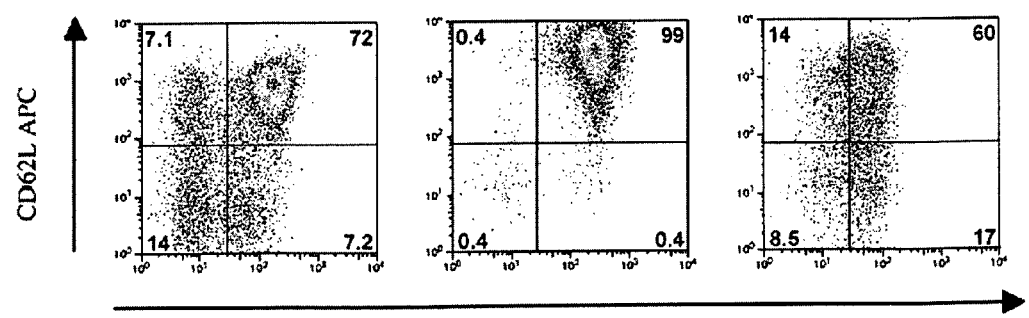

Cell lines were analyzed by flow cytometry for antigens associated with suppressor cell phenotype. Suppressor cell lines were cultured in parallel with CD4$^+$CD25$^-$ derived cell lines which served as conventional T-cell controls. Cell lines were evaluated after 3 weeks of culture, at which time the bead based activation had nearly resolved, and the cells had returned to a more quiescent state. The cell lines maintained a relatively stable phenotype and function for the next 3-5 weeks. The cord derived CD25$^+$ cell lines maintain remarkably uniform expression of multiple antigens, including CD25, intracellular CTLA4, CD27 and CD62L (FIG. 10A). In comparison, the best adult derived suppressor cell lines, generated by the most stringent purification, were slightly heterogeneous for these antigens (FIGS. 10A and 10B).

The cord derived CD25$^+$ cell lines maintained high expression of cell surface CD25 and intracellular CTLA4, an expression pattern considered typical of the T$_{reg}$ phenotype (FIG. 10A). This occurs despite the fact that other activation antigens such as CD69, CD71, and OX40 have returned to baseline expression. The cord derived suppressor cell lines also uniformly express both CD62L and CD27 (FIG. 10B). It was previously demonstrated that within potent adult derived suppressor cell lines, the cells with suppressor function reside within this double positive subset (Godfrey, et al., 2004, Blood 104: 453-461). CD25-derived cells lines also maintain CD27 expression, but at a lower level than CD25$^+$ derived cell lines. This CD27 dim expression pattern was also noted with adult derived CD25-derived cell lines (Godfrey, et al., 2004, Blood 104: 453-461).

Figure 11A:
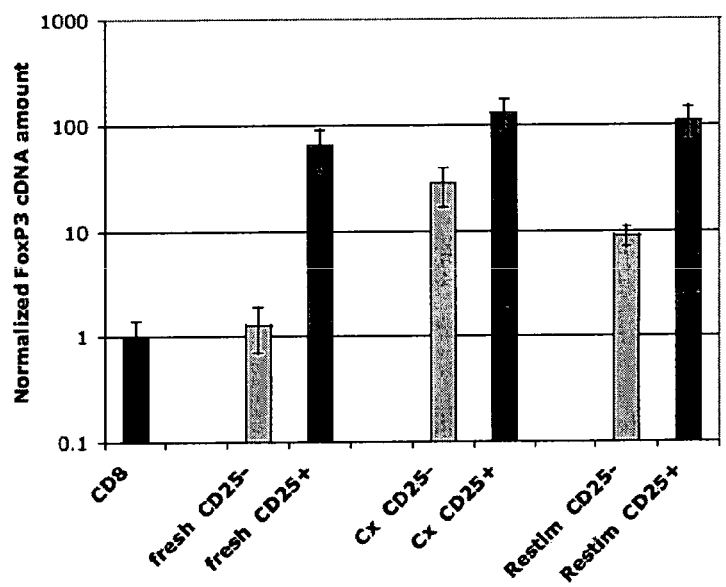
FIGS. 11A and 11B, is an image depicting FoxP3 mRNA and protein expression.

Expression of the transcription factor FoxP3 has been proposed to be the most specific marker for regulatory cells in mice (Ramsdell, et al., 2003, Curr. Opin. Immunol., 15: 718-24). The results disclosed herein demonstrate that the FoxP3 message was expressed at higher levels in CD25$^+$ cells and lines compared to CD25$^-$ T cells and lines. Freshly isolated CD25$^+$ cells from cord blood contained approximately 64 fold more message than CD4$^+$CD25$^-$ cells, or fresh CD8$^+$ T-cells (FIG. 11A). Cultured CD25$^+$ derived cell lines contained 2-4 fold more message than freshly isolated CD25$^+$ cells. Although message levels are low in CD25$^-$ cells on isolation, they increase approximately 25-30 fold on culture. This occurred, even with exhaustive depletion of CD25 dim/positive cells prior to culture (FIG. 11A). Further re-stimulation of the 3-6 week old cell cultures with anti-CD3/CD28 beads did not increase message expression, but rather slightly decreased it in both types of cell lines.

Figure 11B:
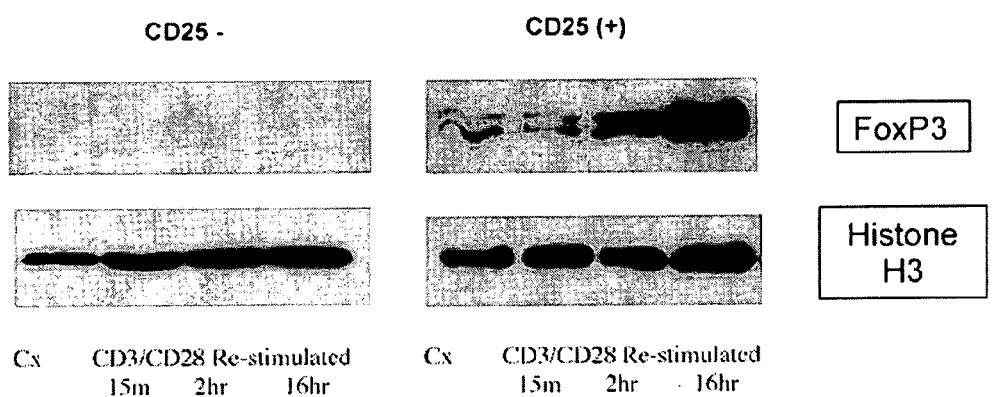

In contrast to the data with mRNA message levels, western blotting with a polyclonal antibody revealed FoxP3 protein expression to be primarily expressed in the CD25$^+$ derived cell lines. Despite expressing message, the CD25$^-$ derived cell lines expressed minimal/background levels of FoxP3 protein (FIG. 11B). Importantly, re-stimulation of the CD25$^+$ cell lines markedly increased FoxP3 protein expression. The increase in FoxP3 protein level occurred despite the minimal change (actual decrease) in message levels. Re-stimulation of CD25$^-$ cells still did not induce FoxP3 protein in CD25$^-$ derived cell lines.

The data disclosed herein demonstrates several interesting facets of FoxP3 mRNA message and protein regulation. Most importantly, FoxP3 protein was found to be relatively specific for CD25$^+$ derived suppressor cells, and was minimally present in CD25$^-$ derived cell lines. We also determined that even exhaustively CD25 depleted CD4$^+$ T-cell derived lines could make significant amounts of FoxP3 message upon culture activation, approximately 20-30 fold more versus resting CD25$^-$ cells. The discordance between FoxP3 mRNA and protein expression indicates that FoxP3 message levels do not necessarily identify or quantify suppressor cells. In addition, re-stimulated CD25$^+$ cells expressed much more FoxP3 protein despite decreased message levels. These findings indicate FoxP3 expression is augmented with activation, and suggest that post-transcriptional mechanisms may contribute to regulation of FoxP3 protein expression.

Figure 12A:
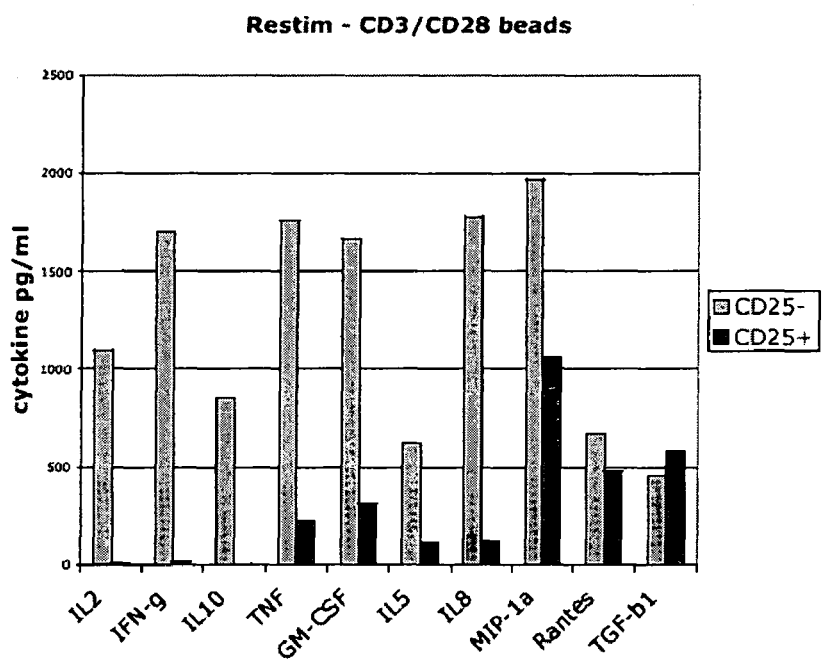
FIGS. 12A through 12D, is a series of images depicting cytokine production defects and cell surface LAP expression 48 hours after re-stimulation of suppressor lines.

Reactivation of Suppressor Cell Lines Induces Minimal Cytokine Production and Enhanced Surface TGF-beta LAP Expression To determine the functional capabilities of the suppressive versus conventional T-cell lines, these cells were evaluated for their potential for cytokine production and cell surface molecule expression after re-stimulation. Cell lines were re-stimulated with anti-CD3/CD28 beads for potent reactivation, and supernatants harvested at defined time-points for analysis of cytokine content by Luminex bead based assay. The CD25$^+$ derived cell lines produced essentially no IL-2, IFN-γ, or IL-10 (FIG. 12A), while control CD25$^-$ derived cell lines produced high levels of these cytokines. The accumulation of TNF, GM-CSF, IL-5, and the chemokine IL-8, was also markedly reduced as compared to control cell lines (FIG. 12A). In contrast, the accumulation of TGF-beta, and the chemokines MIP1a and RANTES were not significantly different between different cell lines.

Figure 12B:
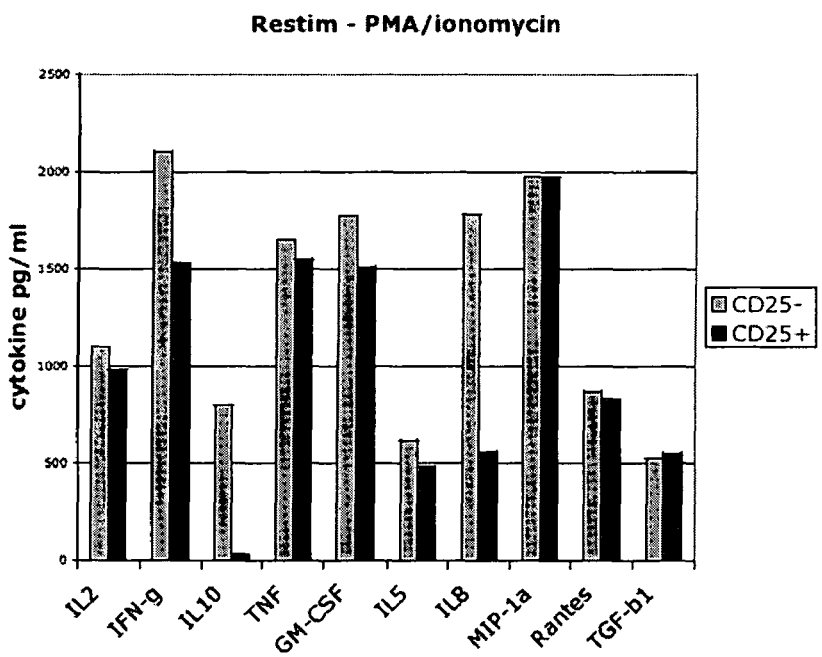

Re-stimulation of the cell lines with pharmacological agents PMA and ionomycin, which can bypass proximal signaling pathways, led to nearly equivalent levels of cytokine production by both the CD25$^+$ and CD25$^-$ derived cell lines (FIG. 12B). Thus, the CD25$^+$ derived cell lines appear to have proximal TCR and CD28 signaling impairments that preclude the normal production of multiple cytokines. In addition, the CD25$^+$ derived cell lines had impaired production of the immunosuppressive cytokine IL-10, which was not restored by PMA/ionomycin stimulation. This suggests that production of IL-10 is probably not a major mechanism of suppression affected by the CD25$^+$ derived cell lines.

Figure 12C:
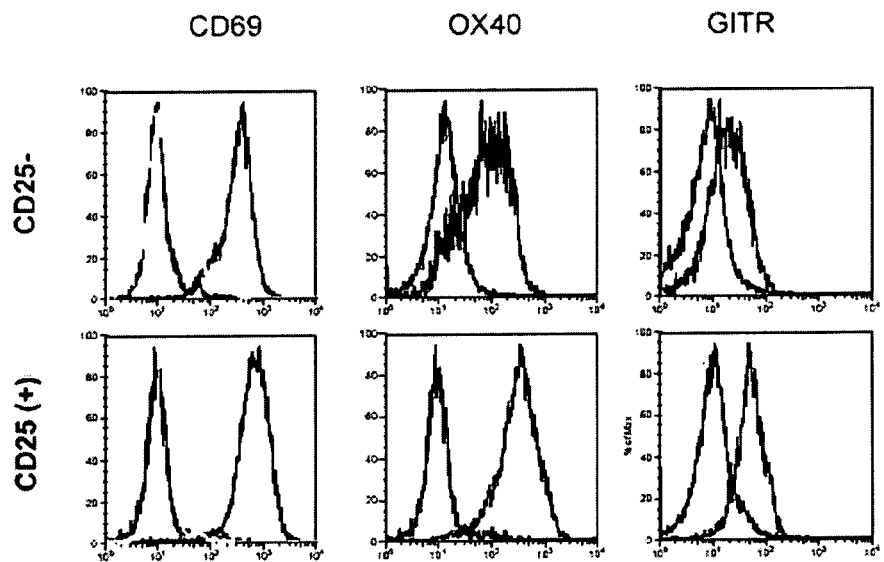

To determine if general activation of cord blood derived CD25$^+$ cell lines was impaired, the expression of cell surface activation antigens was evaluated by flow cytometric analysis. Cell lines were re-stimulated with anti-CD3/CD28 beads and evaluated after overnight culture for CD69, OX40 (CD134), and GITR expression. All three antigens were re-expressed on both the CD25$^+$ and CD25$^-$ derived cell lines (FIG. 12C). The expression of OX40 and GITR appeared slightly enhanced on the CD25$^+$ derived cell lines versus the reactivated CD25$^-$ cell lines (McHugh, et al., 2002, *Immunity* 16: 311-323). Importantly, re-activation of the CD25$^+$ cell lines was relatively intact, as determined by cell surface activation antigen expression analysis, in contrast to the results shown for cytokine accumulation.

Figure 12D:
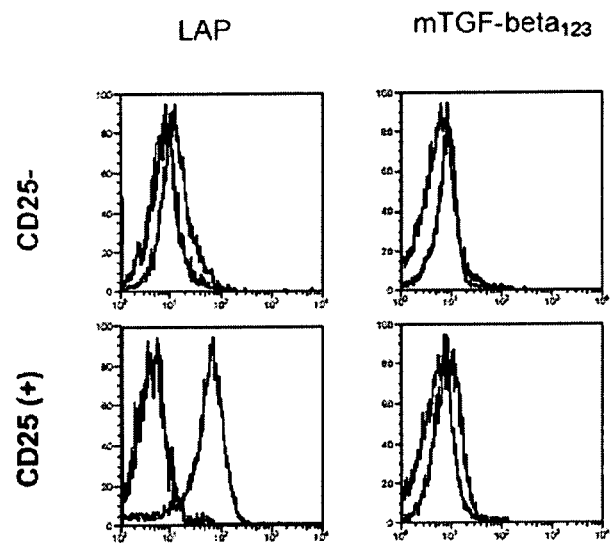

Cell surface expression of the TGF beta latency associated protein (LAP), the TGF beta precursor protein, has been reported to be associated with T$_{reg}$ cells (Nakamura, et al., 2004, *J. Immunol.*, 172: 834-842). In addition, recombinant forms of this protein have been recently reported to partially neutralize suppressor function (Nakamura, et al., 2004, *J. Immunol.*, 172: 834-842). Thus, the expression of LAP on the CD25$^+$ and CD25$^-$ derived cell lines was evaluated. Neither CD25$^+$ or CD25$^-$ lines expressed this protein after culture for 3-6 weeks, however, after re-stimulation with anti-CD3/CD28 beads there was a distinct expression of cell surface LAP on the CD25$^+$ derived cell lines (FIG. 12D), but not the CD25$^-$ derived cell lines. Cell surface expression of TGF-beta was not detectable.

Suppressor cells were found (on re-stimulation) to have limited potential for cytokine production. There was a profound lack of IL-2, IFN-gamma, and IL-10 production, and a markedly reduced ability to produce GM-CSF, TNF, IL-5, and IL-8. In contrast, activation as assessed by up-regulated expression of CD69, OX40, and GITR, and production of MIP-1a and RANTES, was generally intact. Interestingly, cytokine production ability was restored with PMA/ionomycin stimulation. This indicates a partial proximal TCR signaling block in the suppressor cells, and is consistent with the anergic response characteristics of the suppressor cells to TCR stimulation.

Figure 13A:
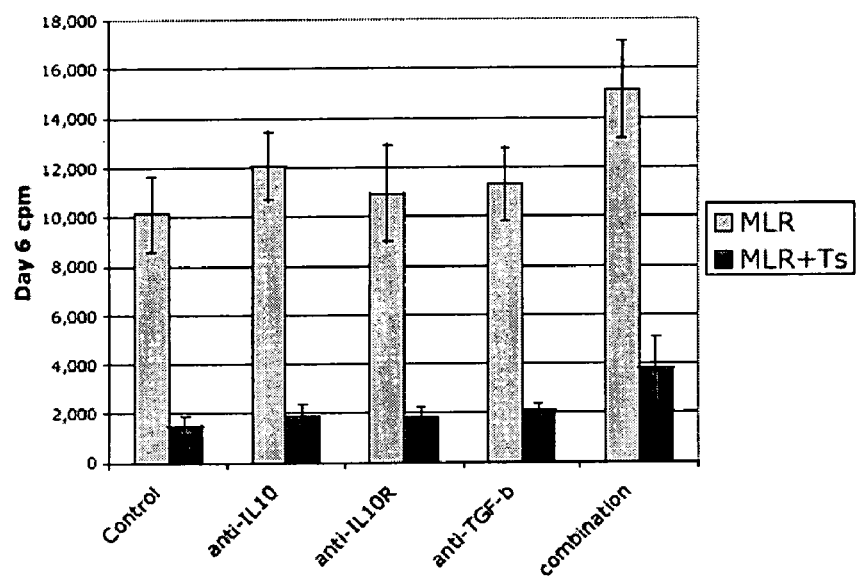
FIGS. 13A through 13D, is a series of images depicting a screen of multiple neutralizing antibodies and fusion proteins for functional effects on the suppression of a CD4+ T cell-DC MLR.
Figure 13B:
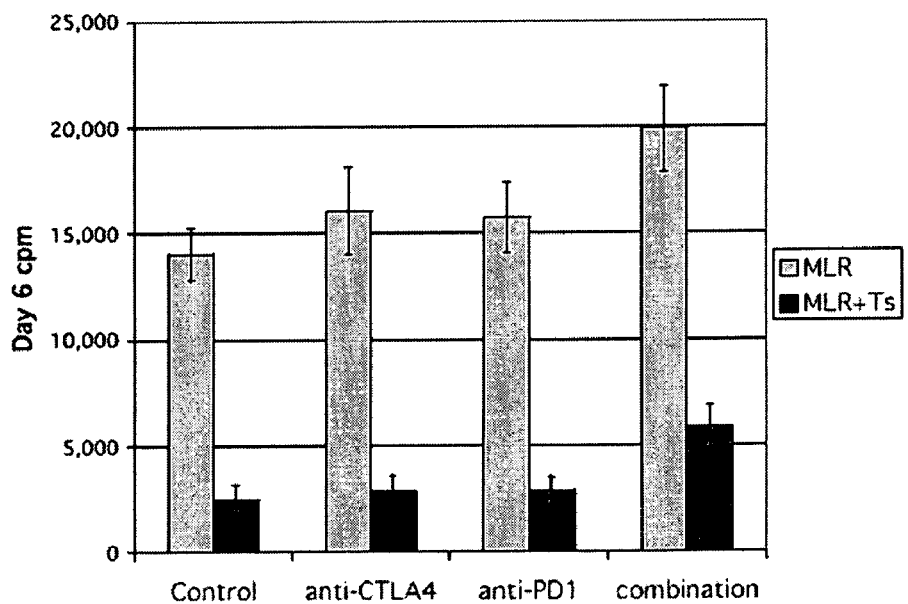
Figure 13C:
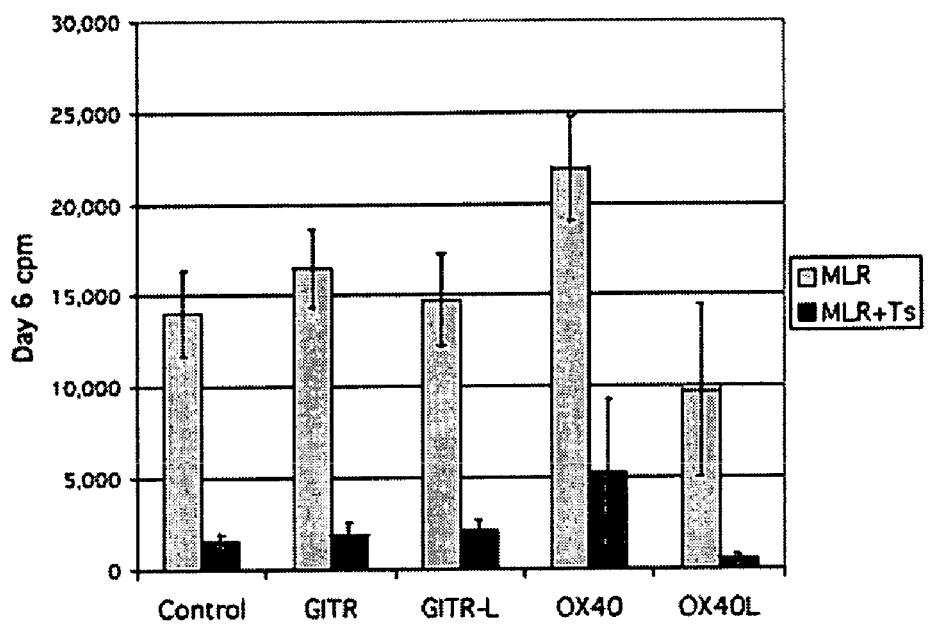

Cultured Suppressor Cells Function by an Unknown Mechanism Independent of IL-10, TGF-beta, and Multiple Costimulatory Molecules To determine if the cultured suppressor cell lines work through known soluble immunosuppressive or cell surface negative regulatory proteins, DC-MLR suppressor assays were treated with neutralizing or blocking monoclonal antibodies. Assays were evaluated for the reversal of suppression by resumption of proliferation. Initially antibodies to IL-10, IL-10R, and TGF-$_{beta\ 1,2,3}$, were tested alone or in various combinations with minimal effect. Only by combining all three antibodies at high doses (30 μg/ml), were modest and probably non-specific effects seen (FIG. 13A). Treated control cultures also evidenced increased proliferation. Antibodies to the negative costimulatory signaling molecules CTLA4 and PD1 were also tested and found to have essentially no effect on their own, but again only in combination was a marginal effect on suppression noted (FIG. 13B). Agonist antibodies to receptors whose signaling is reported to abrogate or diminish suppressor function of resting murine T$_{reg}$, GITR (Ji, et al., 2004, *J. Immunol.*, 172: 5823-5827) and OX40 (CD134) (Takeda, et al., 2004, *J. Immunol.*, 172: 3580-3589), were tested and found to have minimal effects on the cultured suppressor cells. Agonist antibody to OX40 appeared to impair suppressor function in some donors more than others (mean 32% reversion, n=6, range 15-75%). However, agonist antibody to OX40 also increased the magnitude of the control MLR, in approximate correlation with the magnitude of reversion of suppression (FIG. 13C). Antibodies to OX40L inhibited the MLR (with donor variability) but also increased the apparent magnitude of suppression (mean 96% suppression, n=5, range 90-98%, versus 90% for control cultures) (FIG. 7C).

Figure 13D:
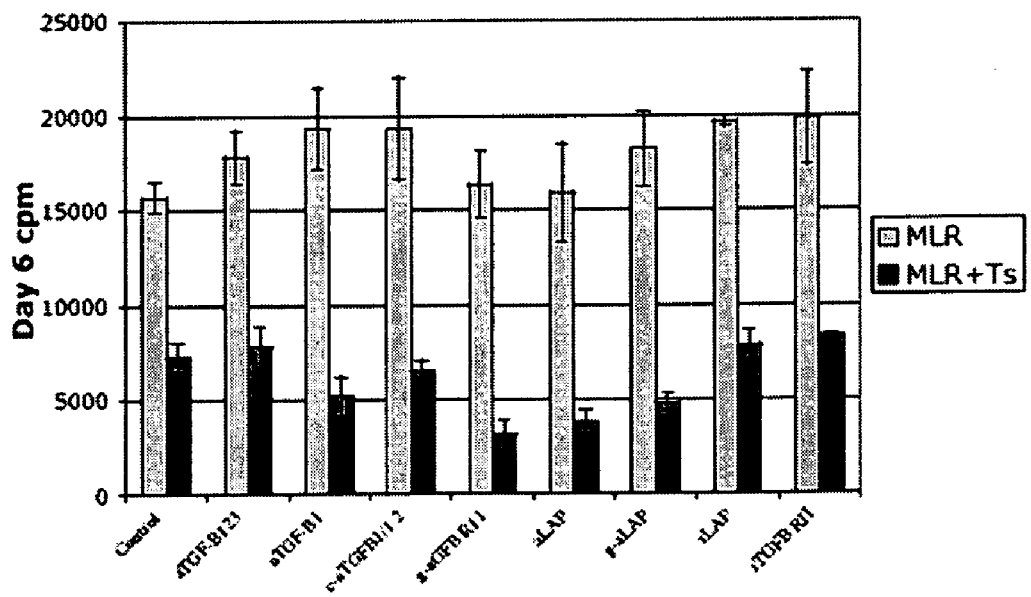

Because of the specific increased cell surface LAP expression on reactivated cultured suppressor cells, and the suggested importance of TGF-beta to suppressor function (Nakamura, et al., 2004, *J. Immunol.*, 172: 834-842; Chen, et al., 2003, *Cytokine Growth Factor Rev.*, 14: 85-89), multiple antagonists of the TGF beta pathway were evaluated. Neutralizing antibodies, both monoclonal and polyclonal, soluble receptors, recombinant LAP, and antibody to LAP were all tested in the MLR system. All reagents alone or in multiple combinations failed to reverse suppression mediated by the cultured T$_{reg}$ cell lines. Experiments were conducted with a lower number of suppressor cells, specifically a 1:10 responder stimulator ratio, to minimize the potency of the suppression, resulting in approximately 50% inhibition in control MLR. Even under these conditions, minimal effects were noted (FIG. 13D).

These studies demonstrate that cord blood, when compared to adult blood, is an improved source for T$_{reg}$ isolation and culture. Potent suppressive cell lines were isolated from virtually every donor, and these results were obtained with a straightforward direct MACS based purification. Flow cytometric profiles of antigen expression on cord blood T$_{reg}$ cell lines were surprisingly uniform. This system was used to further characterize suppressor cell phenotype and function.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of generating a regulatory T cell (T$_{reg}$ cell) suppressor cell line, wherein said T$_{reg}$ suppressor cell line suppresses T cell proliferation in a mixed lymphocyte reaction by a factor of at least 95% at a ratio of 1:32 (T$_{reg}$: T cell), said method comprising:

a) isolating a population of mononuclear cells from a human umbilical cord blood sample;

b) contacting said population of mononuclear cells with an antibody that specifically binds CD25 under conditions suitable for formation of a mononuclear cell-antibody complex;
c) substantially separating said mononuclear cell-antibody complex from said population of mononuclear cells; thereby isolating a population of phenotypically CD25$^+$ CD45RA$^+$ blood cells;
d) expanding said isolated population of CD25$^+$ cells in the presence of anti-CD3/CD28 antibody coated beads;
e) activating said expanded population of CD25$^+$ cells in the presence of IL-2; and
f) substantially separating said activated population of CD25$^+$ cells; thereby generating a suppressor cell line that suppresses T cell proliferation in a mixed lymphocyte reaction by at least 95% when at a ratio of 1:32 ($T_{reg}$: T cell).

2. The method of claim 1, wherein said antibody is selected from the group consisting of an isolated antibody, a biological sample comprising an antibody, an antibody bound to a physical support and a cell-bound antibody.

3. The method of claim 2, wherein said antibody is selected from the group consisting of a polyclonal antibody, a monoclonal antibody, a humanized antibody, a synthetic antibody, a biologically active fragment of an antibody, and combinations thereof.

4. The method of claim 3, wherein said biologically active fragment is selected from the group consisting of an Fab fragment, a F(ab')$_2$ fragment, a Fv fragment, and an scFv fragment.

5. The method of claim 2, wherein said physical support is selected from the group consisting of a microbead, a magnetic bead, an absorption column and an adsorption membrane.

6. The method of claim 1, wherein said mononuclear cell-antibody complex is substantially separated from said population of mononuclear cells by a method selected from the group consisting of fluorescence activated cell sorting (FACS) and magnetic activated cell sorting (MACS).

7. The method of claim 1, wherein steps b) and c) are repeated.

* * * * *

UNITED STATES PATENT AND TRADEMARK OFFICE
CERTIFICATE OF CORRECTION

PATENT NO. : 9,187,727 B2
APPLICATION NO. : 13/544218
DATED : November 17, 2015
INVENTOR(S) : Wayne R. Godfrey and Carl June Page 1 of 1

It is certified that error appears in the above-identified patent and that said Letters Patent is hereby corrected as shown below:

In the Specification

In column 1, after the title, GOVERNMENT INTERESTS, please replace the paragraph at lines 15-19 with the following paragraph:

--This invention was made with government support under grant number R01 AI034495 and R37 HL056067 awarded by the National Institutes of Health. The government has certain rights in the invention.--

Signed and Sealed this
Twenty-eighth Day of June, 2016

Michelle K. Lee
*Director of the United States Patent and Trademark Office*